United States Patent
Inoue et al.

(10) Patent No.: US 11,584,852 B2
(45) Date of Patent: Feb. 21, 2023

(54) COMPOUND AND COLORED RESIN COMPOSITION

(71) Applicant: SUMITOMO CHEMICAL COMPANY, LIMITED, Tokyo (JP)

(72) Inventors: Keisuke Inoue, Osaka (JP); Yutaka Kawanishi, Osaka (JP); Tetsuo Akasaka, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/968,729

(22) PCT Filed: Feb. 19, 2019

(86) PCT No.: PCT/JP2019/005970
§ 371 (c)(1),
(2) Date: Aug. 10, 2020

(87) PCT Pub. No.: WO2019/163732
PCT Pub. Date: Aug. 29, 2019

(65) Prior Publication Data
US 2021/0002487 A1    Jan. 7, 2021

(30) Foreign Application Priority Data

Feb. 26, 2018  (JP) .............................. JP2018-032370
Jul. 27, 2018  (JP) .............................. JP2018-141796

(51) Int. Cl.
| | |
|---|---|
| *C09B 57/00* | (2006.01) |
| *C08K 5/29* | (2006.01) |
| *G02B 5/22* | (2006.01) |
| *C07C 215/82* | (2006.01) |
| *C07C 217/92* | (2006.01) |

(52) U.S. Cl.
CPC .......... *C09B 57/007* (2013.01); *C07C 215/82* (2013.01); *C07C 217/92* (2013.01); *C08K 5/29* (2013.01); *G02B 5/223* (2013.01)

(58) Field of Classification Search
CPC ... C09B 57/007; C07C 215/82; C07C 217/92; G02B 5/223; C08K 5/29
See application file for complete search history.

(56) References Cited

U.S. PATENT DOCUMENTS

| | | | |
|---|---|---|---|
| 2007/0123707 A1 | 5/2007 | Zapf et al. | |
| 2014/0264202 A1* | 9/2014 | Nagaya .................. | G02B 5/208 252/587 |

FOREIGN PATENT DOCUMENTS

| | | |
|---|---|---|
| CN | 1791606 A | 6/2006 |
| CN | 108276334 A | 7/2018 |
| JP | 2009-036811 A | 2/2009 |
| JP | 2009036811 A * | 2/2009 ............. G03G 9/087 |
| JP | 2015-086379 A | 5/2015 |
| JP | 2015086379 A * | 5/2015 ............. C09B 23/00 |
| WO | WO-2004/101581 A2 | 11/2004 |

OTHER PUBLICATIONS

Andrea M. Della Pelle, Paul J. Homnick, Youngju Bae, Paul M. Lahti, and S. Thayumanavan, Effect of Substituents on Optical Properties and Charge-Carrier Polarity of Squaraine Dyes, J. Phys. Chem. C 2014, 118, 1793-1799 (Year: 2014).*

Ferguson et al., "Palladium-Catalyzed Intra- and Intermolecular C—H Arylation Using Mesylates: Synthetic Scope and Mechanistic Studies," American Chemical Society Catalysis, vol. 4, No. 7, 2014, pp. 2395-2401.

Schmidt et al., "Halogen-Activated Smiles Rearrangement. 2," Journal of Organic Chemistry, vol. 49, No. 9, 1984, pp. 1664-1666.

Pelle et al., "Effect of Substituents on Optical Properties and Charge-Carrier Polarity of Squaraine Dyes," The Journal of Physical Chemistry C, vol. 118, No. 4, 2014, pp. 1793-1799.

International Searching Authority, "International Search Report," issued in connection with International Patent Application No. PCT/JP2019/005970, dated May 7, 2019.

International Searching Authority, "Written Opinion," issued in connection with International Patent Application No. PCT/JP2019/005970, dated May 7, 2019.

Registry (SIN) [online], Oct. 29, 1988 (retrieved on Apr. 18, 2019), CAS Registry No. 117124-32-0.

(Continued)

*Primary Examiner* — Bijan Ahvazi
(74) *Attorney, Agent, or Firm* — Foley & Lardner LLP

(57) ABSTRACT

An object of the present invention is to provide a novel squarylium dye that can achieve an equivalent chromaticity value of even a colored resin composition having a low content of the squarylium dye as compared with a colored resin composition comprising a conventional squarylium dye. The present invention provides a compound represented by the formula (I) wherein $R^4$ to $R^4$ each independently represent a hydrogen atom or the like; $R^5$ to $R^8$ each independently represent a hydrogen atom or the like; $R^9$ and $R^{10}$ each independently represent a monovalent saturated hydrocarbon group having 1 to 20 carbon atoms or the like; $R^{11}$ and $R^{12}$ each independently represent a halogen atom or an alkyl halide group having 1 to 6 carbon atoms; and m1 and m2 each independently represent an integer of 1 to 5.

[Formula 1]

(I)

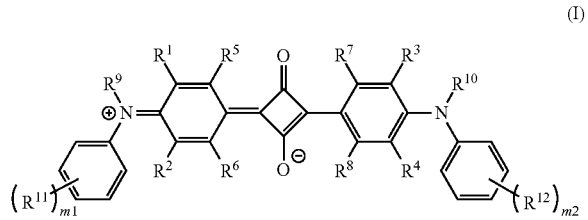

3 Claims, No Drawings

(56) References Cited

OTHER PUBLICATIONS

Registry (SIN) [online], Dec. 24, 2008 (retrieved on Apr. 18, 2019), CAS Registry No. 1089311-76-1, Nov. 7, 2008 (retrieved on Apr. 18, 2019), CAS Registry No. 1071597.29.9.
Office Action dated Apr. 30, 2021 for corresponding Chinese Patent Application No. 201980014502.0.
Schmidt et al; "Halogen-Activated Smiles Rearrangement. 2"; Journal of Organic Chemistry; 1984; 49; pp. 1664-1666.
Japanese Office Action dated May 2, 2022 issued in corresponding Japanese Application No. JP2018-141796.

* cited by examiner

COMPOUND AND COLORED RESIN COMPOSITION

CROSS-REFERENCE TO RELATED APPLICATIONS

The present application claims priority under 37 U.S.C. § 371 to International Patent Application No. PCT/JP2019/005970, filed Feb. 19, 2019, which claims priority to and the benefit of Japanese Patent Application Nos. 2018-032370, filed on Feb. 26, 2018, and 2018-141796, filed on Jul. 27, 2018. The contents of these applications are hereby incorporated by reference in their entireties.

TECHNICAL FIELD

The present invention relates to a novel compound and a colored resin composition.

BACKGROUND ART

In colored curable resin compositions, it is known that squarylium dyes are used as colorants. Patent Literature 1 has proposed a squarylium dye represented by a specific general formula.

CITATION LIST

Patent Literature

Patent Literature 1: Japanese Patent Laid-Open No. 2015-86379

SUMMARY OF INVENTION

Technical Problem

An object of the present invention is to provide a novel squarylium dye that can achieve an equivalent chromaticity value of even a colored resin composition having a low content of the squarylium dye as compared with a colored resin composition comprising a conventional squarylium dye. Another object of the present invention is to provide a precursor of the novel squarylium dye and a method for producing the novel squarylium dye.

Solution to Problem

The present invention provides the following [1] to [6]:
[1] A compound represented by the formula (I):

[Formula 1]

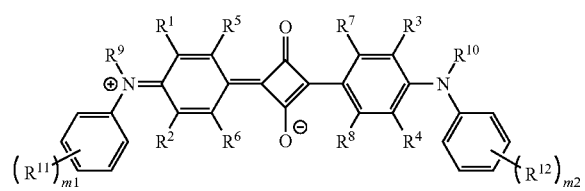

(I)

wherein
$R^1$ to $R^4$ each independently represent a hydrogen atom, a halogen atom, a hydroxy group or a monovalent saturated hydrocarbon group having 1 to 20 carbon atoms, wherein a hydrogen atom contained in the saturated hydrocarbon group is optionally replaced with a halogen atom, a hydroxy group or $-N(R^a)_2$, and $-CH_2-$ contained in the saturated hydrocarbon group is optionally replaced with $-O-$ or $-S-$; $R^a$ represents a hydrogen atom or an alkyl group having 1 to 8 carbon atoms;

$R^5$ to $R^8$ each independently represent a hydrogen atom or a hydroxy group;

$R^9$ and $R^{10}$ each independently represent a monovalent saturated hydrocarbon group having 1 to 20 carbon atoms, wherein a hydrogen atom contained in the saturated hydrocarbon group is optionally replaced with a halogen atom, a hydroxy group, $-N(R^b)_2$ or an aromatic hydrocarbon group having 6 to 20 carbon atoms and optionally having a substituent, and $-CH_2-$ contained in the saturated hydrocarbon group is optionally replaced with $-O-$, $-S-$, $-NR^b-$ or $-C(=O)-$; $R^b$ represents a hydrogen atom or an alkyl group having 1 to 8 carbon atoms;

$R^{11}$ and $R^{12}$ each independently represent a halogen atom or an alkyl halide group having 1 to 6 carbon atoms;

m1 and m2 each independently represent an integer of 1 to 5; and when m1 is 2 or larger, a plurality of $R^{11}$ are the same as or different from each other, and when m2 is 2 or larger, a plurality of $R^{12}$ are the same as or different from each other.

[2] A colored resin composition comprising a colorant comprising a compound according to [1], and a resin.

[3] A color filter formed from a colored resin composition according to [2].

[4] A solid-state imaging device comprising a color filter according to [3].

[5] A method for producing a compound according to [1], comprising reacting a compound represented by the following formula (IV-1) with 3,4-dihydroxy-3-cyclobutene-1,2-dione, or reacting a compound represented by the following formula (IV-1) with 3,4-dihydroxy-3-cyclobutene-1,2-dione to obtain a compound represented by the following formula (V-1), and reacting the obtained compound represented by the following formula (V-1) with a compound represented by the following formula (IV-2):

[Formula 2]

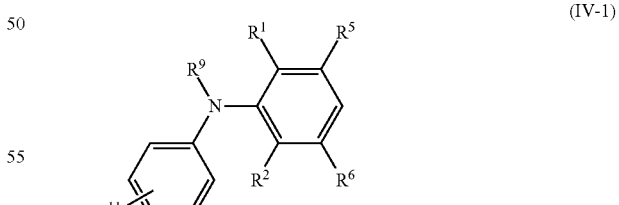

(IV-1)

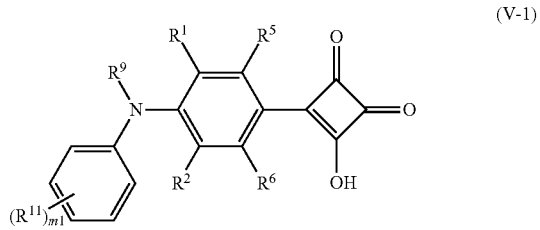

(V-1)

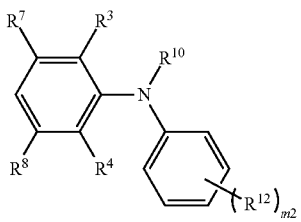

(IV-2)

wherein $R^1$ to $R^4$ each independently represent a hydrogen atom, a halogen atom, a hydroxy group or a monovalent saturated hydrocarbon group having 1 to 20 carbon atoms, wherein a hydrogen atom contained in the saturated hydrocarbon group is optionally replaced with a halogen atom, a hydroxy group or —N($R^a$)$_2$, and —CH$_2$— contained in the saturated hydrocarbon group is optionally replaced with —O— or —S—; $R^a$ represents a hydrogen atom or an alkyl group having 1 to 8 carbon atoms;

$R^5$ to $R^8$ each independently represent a hydrogen atom or a hydroxy group;

$R^9$ and $R^{10}$ each independently represent a monovalent saturated hydrocarbon group having 1 to 20 carbon atoms, wherein a hydrogen atom contained in the saturated hydrocarbon group is optionally replaced with a halogen atom, a hydroxy group, —N($R^b$)$_2$ or an aromatic hydrocarbon group having 6 to 20 carbon atoms and optionally having a substituent, and —CH$_2$— contained in the saturated hydrocarbon group is optionally replaced with —O—, —S—, —N$R^b$— or —C(=O)—; $R^b$ represents a hydrogen atom or an alkyl group having 1 to 8 carbon atoms;

$R^{11}$ and $R^{12}$ each independently represent a halogen atom or an alkyl halide group having 1 to 6 carbon atoms;

m1 and m2 each independently represent an integer of 1 to 5; and when m1 is 2 or larger, a plurality of $R^{11}$ are the same as or different from each other, and when m2 is 2 or larger, a plurality of $R^{12}$ are the same as or different from each other.

[6] A compound represented by the formula (IV-1) according to [5].

Advantageous Effects of Invention

A colored resin composition comprising a compound represented by the formula (I) can decrease the content of a colorant for achieving the same chromaticity value as that of a colored resin composition comprising a conventional squarylium dye. Such a decreased content of the colorant in the colored resin composition permits thinning of the resulting cured product of the colored resin composition and enlarges the range of designability as to a resin, etc. for use in the colored resin composition.

DESCRIPTION OF EMBODIMENTS

<Compound>

The compound of the present invention is a compound represented by the formula (I) (hereinafter, also referred to as the compound (I)). The compound (I) is represented by the formula (I) and further includes, for example, tautomers having resonance structures as represented by the formulas given below. The compound (I) includes every tautomer.

[Formula 3]

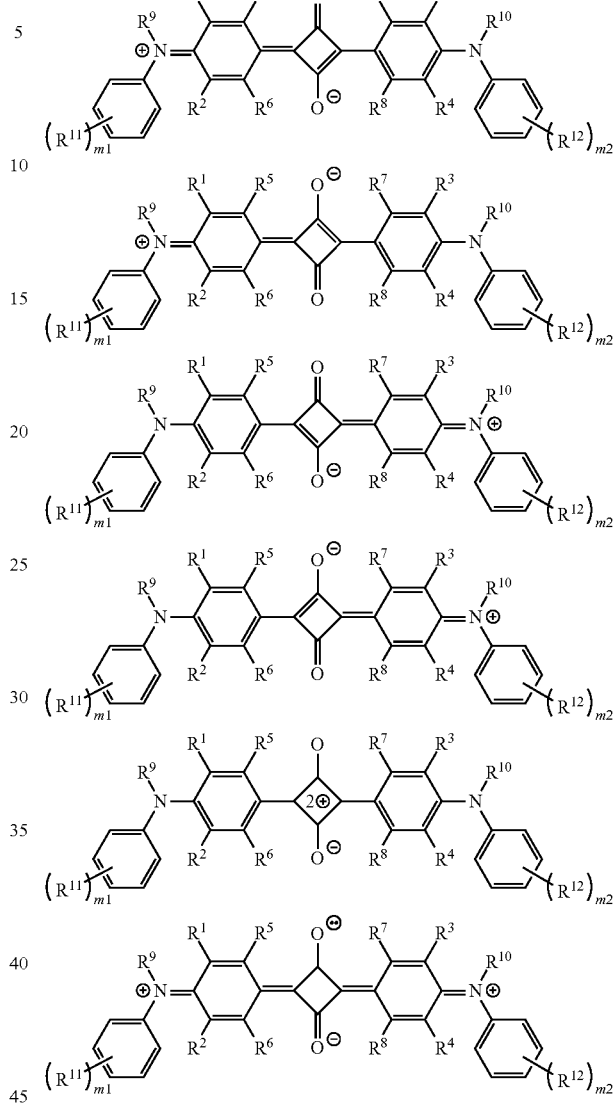

In the formula (I), examples of the halogen atom represented by $R^1$ to $R^4$ include a fluorine atom, a chlorine atom, a bromine atom and an iodine atom.

Examples of the monovalent saturated hydrocarbon group having 1 to 20 carbon atoms represented by $R^1$ to $R^4$ include: linear alkyl groups having 1 to 20 carbon atoms, such as a methyl group, an ethyl group, a propyl group, a butyl group, a pentyl group, a hexyl group, a heptyl group, an octyl group, a nonyl group, a decyl group, a dodecyl group, a hexadecyl group and an icosyl group; branched alkyl groups having 3 to 20 carbon atoms, such as an isopropyl group, an isobutyl group, a sec-butyl group, a tert-butyl group, an isopentyl group, a neopentyl group and a 2-ethylhexyl group; and alicyclic saturated hydrocarbon groups having 3 to 20 carbon atoms, such as a cyclopropyl group, a cyclopentyl group, a cyclohexyl group, a cycloheptyl group, a cyclooctyl group and a tricyclodecyl group.

Examples of the group in which a hydrogen atom contained in the monovalent saturated hydrocarbon group having 1 to 20 carbon atoms represented by $R^1$ to $R^4$ is replaced with a halogen atom, a hydroxy group or —N(R$^a$)$_2$ include groups represented by the formulas given below. In this context, examples of —N(R$^a$)$_2$ include a methylamino group, an ethylamino group, a n-propylamino group, a n-butylamino group, a n-pentylamino group, a dimethylamino group, a diethylamino group, a dibutylamino group, and a methylethylamino group. Two R$^a$ are the same as or different from each other. In the following formulas, * represents a bond.

[Formula 4]

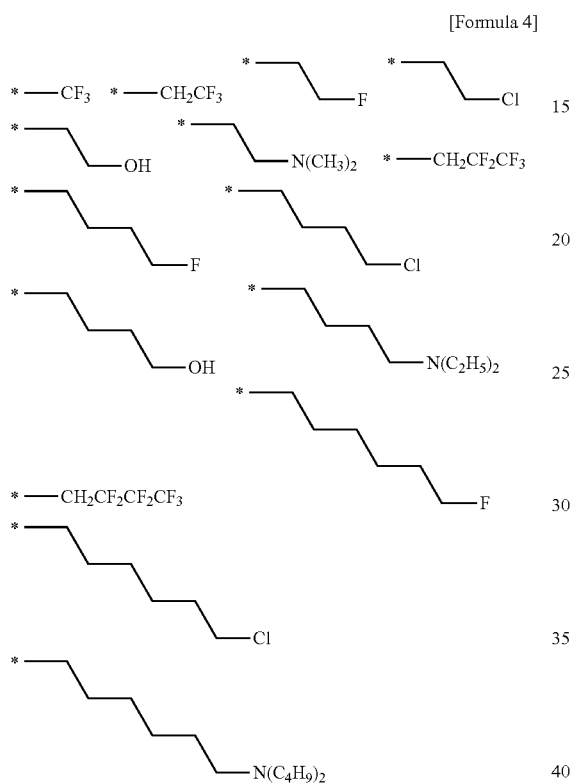

Examples of the group in which —CH$_2$— contained in the monovalent saturated hydrocarbon group having 1 to 20 carbon atoms represented by R$^1$ to R$^4$ is replaced with —O— or —S— include groups represented by the formulas given below. In the following formulas, * represents a bond.

[Formula 5]

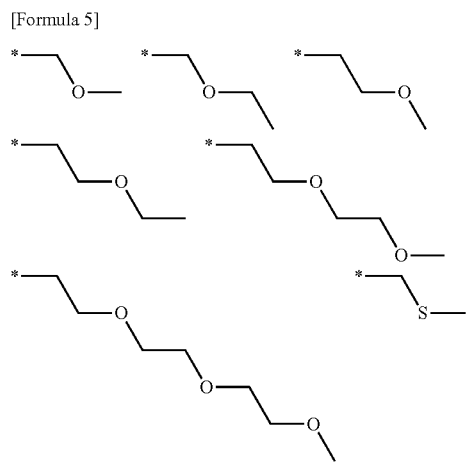

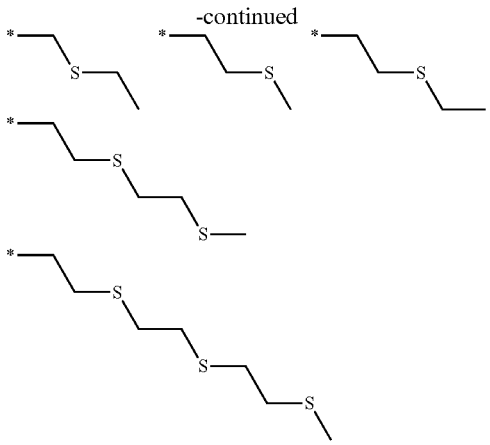

Examples of the monovalent saturated hydrocarbon group having 1 to 20 carbon atoms represented by R$^9$ and R$^{10}$ include: linear alkyl groups having 1 to 20 carbon atoms, such as a methyl group, an ethyl group, a propyl group, a butyl group, a pentyl group, a hexyl group, a heptyl group, an octyl group, a nonyl group, a decyl group, a dodecyl group, a hexadecyl group and an icosyl group; branched alkyl groups having 3 to 20 carbon atoms, such as an isopropyl group, an isobutyl group, a sec-butyl group, a tert-butyl group, an isopentyl group, a neopentyl group and a 2-ethylhexyl group; and alicyclic saturated hydrocarbon groups having 3 to 20 carbon atoms, such as a cyclopropyl group, a cyclopentyl group, a cyclohexyl group, a cycloheptyl group, a cyclooctyl group and a tricyclodecyl group.

Examples of the group in which a hydrogen atom contained in the monovalent saturated hydrocarbon group having 1 to 20 carbon atoms represented by R$^9$ and R$^{10}$ is replaced with a halogen atom, a hydroxy group or —N(R$^b$)$_2$ include groups represented by the formulas given below. In this context, examples of the halogen atom include a fluorine atom, a chlorine atom, a bromine atom and an iodine atom. Examples of —N(R$^b$)$_2$ include —NHCH$_3$, —NHCH$_2$CH$_3$, —NHCH$_2$CH$_2$CH$_3$, —NHCH$_2$CH$_2$CH$_2$CH$_3$, —N(CH$_3$)$_2$, —N(CH$_3$)$_2$, —N(CH$_2$CH$_3$)$_2$, and —N(CH$_2$CH$_2$CH$_2$CH$_3$)$_2$. Two R$^b$ are the same as or different from each other. In the following formulas, * represents a bond.

[Formula 6]

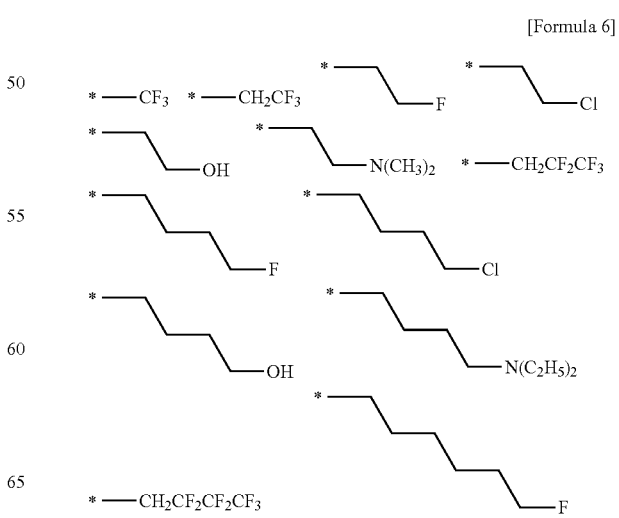

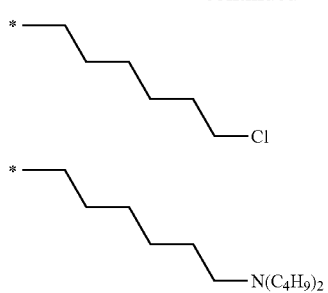

Examples of the aromatic hydrocarbon group having 6 to 20 carbon atoms and optionally having a substituent with which a hydrogen atom contained in the monovalent saturated hydrocarbon group having 1 to 20 carbon atoms represented by $R^9$ and $R^{10}$ is optionally replaced include compounds represented by the formulas given below. In the following formulas, * represents a bond.

[Formula 7]

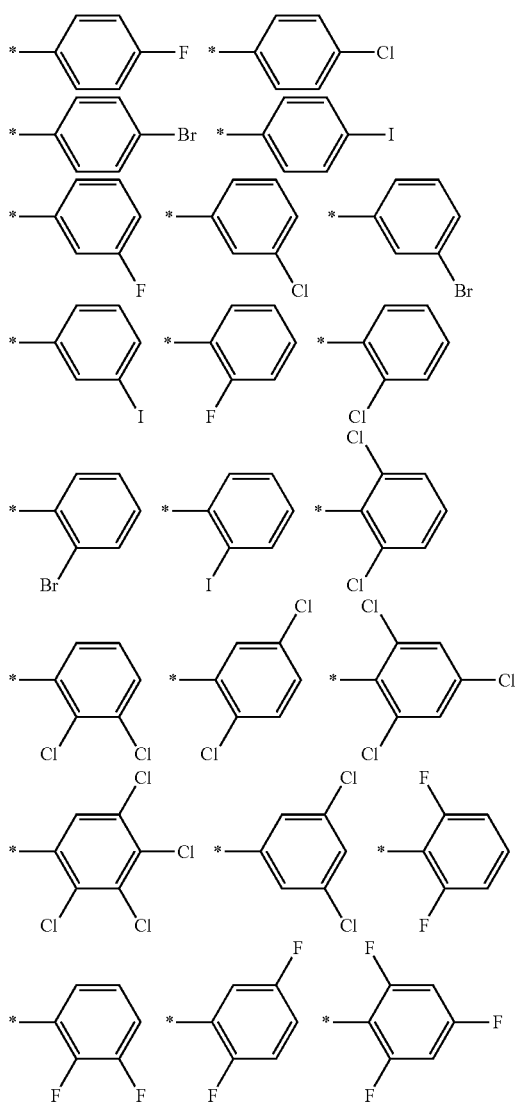

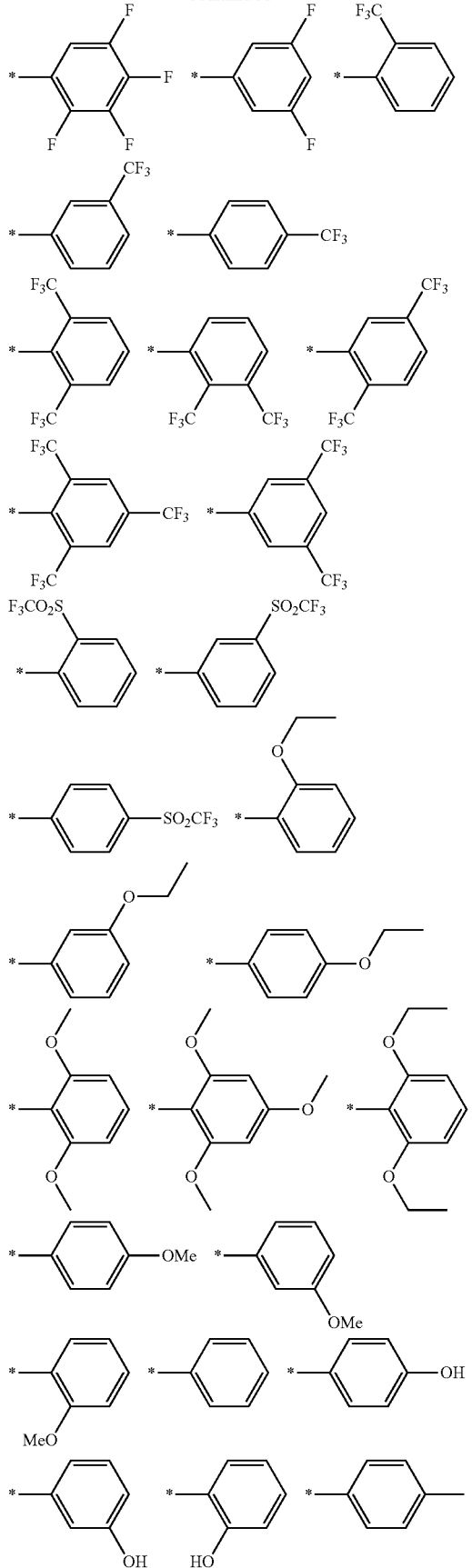

-continued

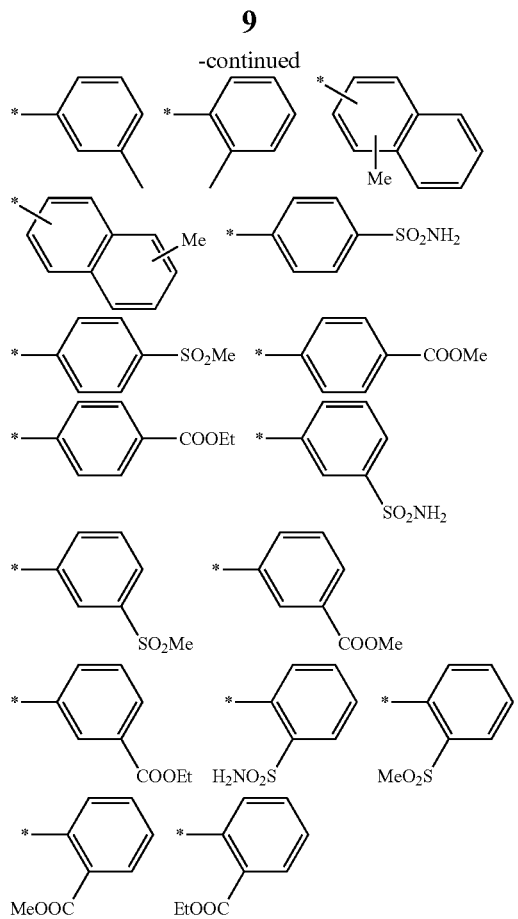

Examples of the group in which a hydrogen atom contained in the monovalent saturated hydrocarbon group having 1 to 20 carbon atoms represented by $R^9$ and $R^{10}$ is replaced with an aromatic hydrocarbon group having 6 to 20 carbon atoms and optionally having a substituent include groups represented by the formulas given below. In the following formulas, * represents a bond.

[Formula 8]

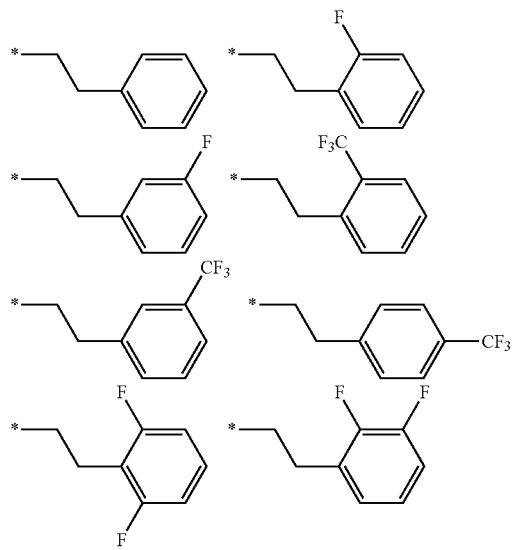

-continued

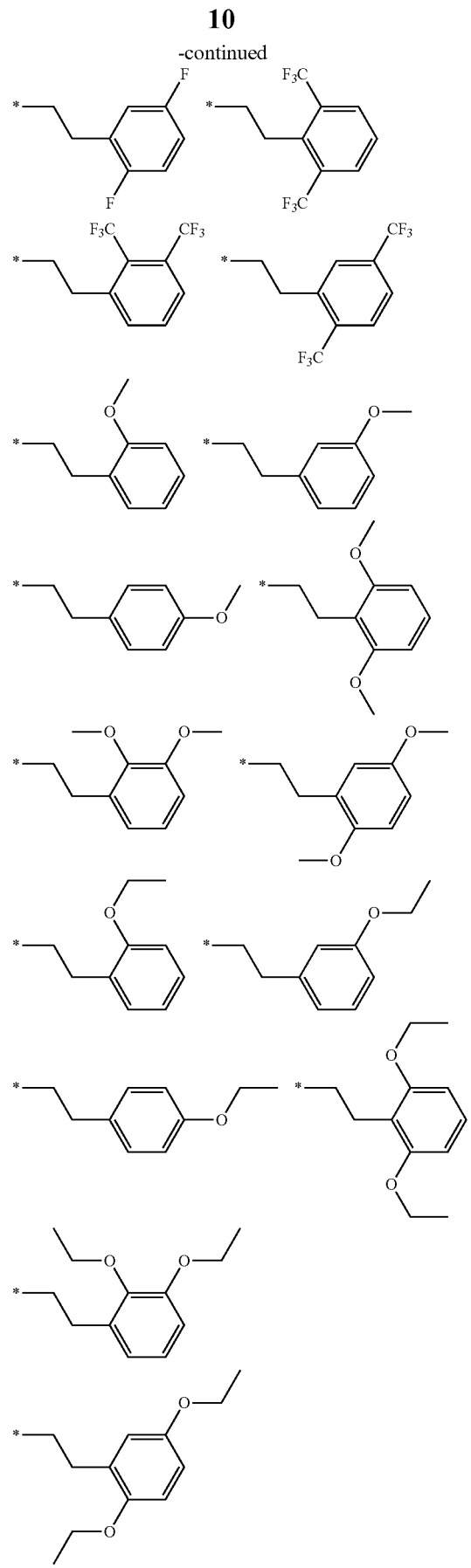

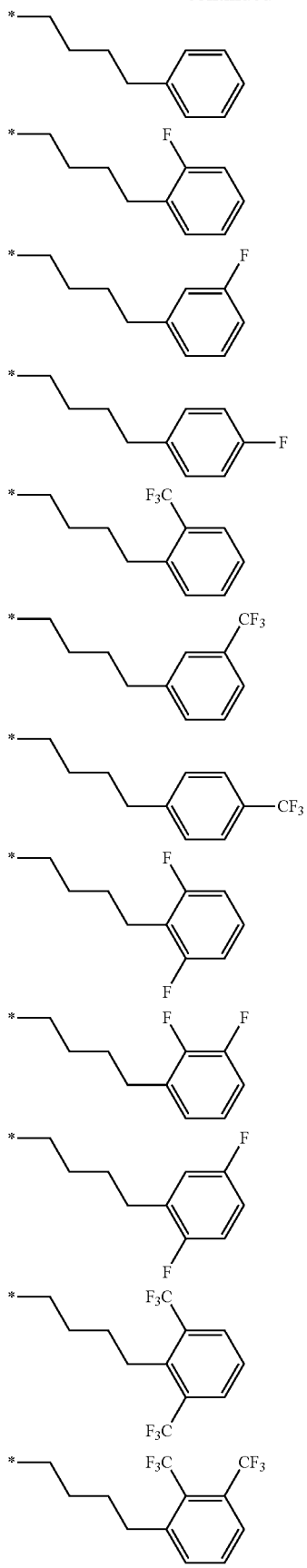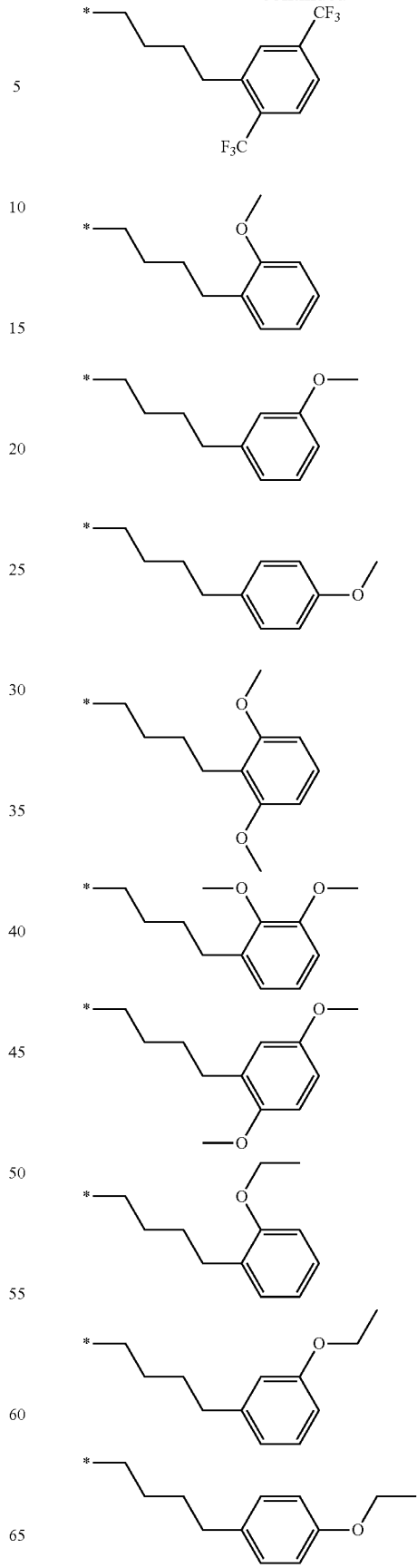

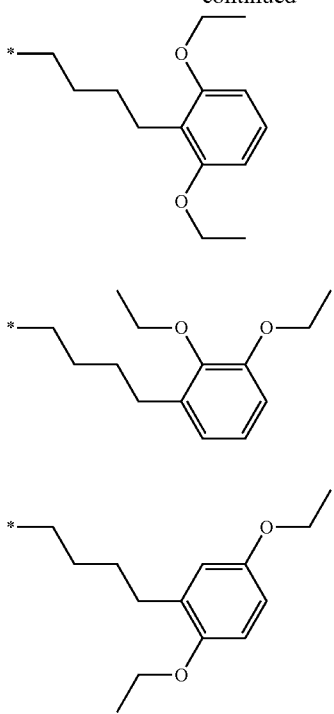
Examples of the group in which —CH$_2$— contained in the monovalent saturated hydrocarbon group having 1 to 20 carbon atoms represented by R$^9$ and R$^{10}$ is replaced with —O—, —S—, —NR$^b$— or —C(=O)— include groups represented by the formulas given below. In the following formulas, * represents a bond.
[Formula 9]
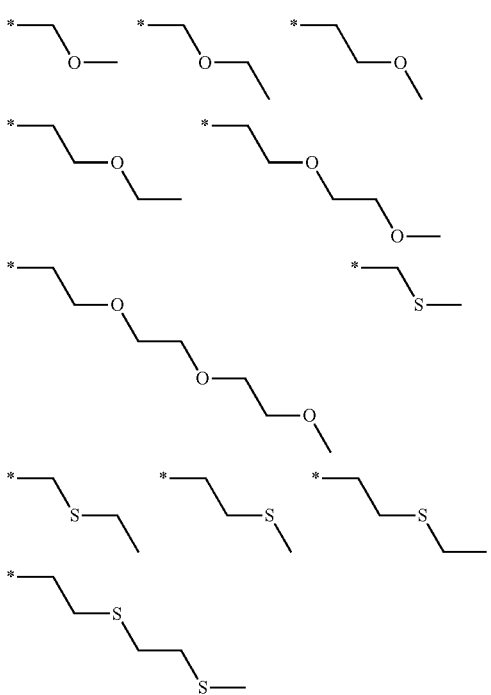
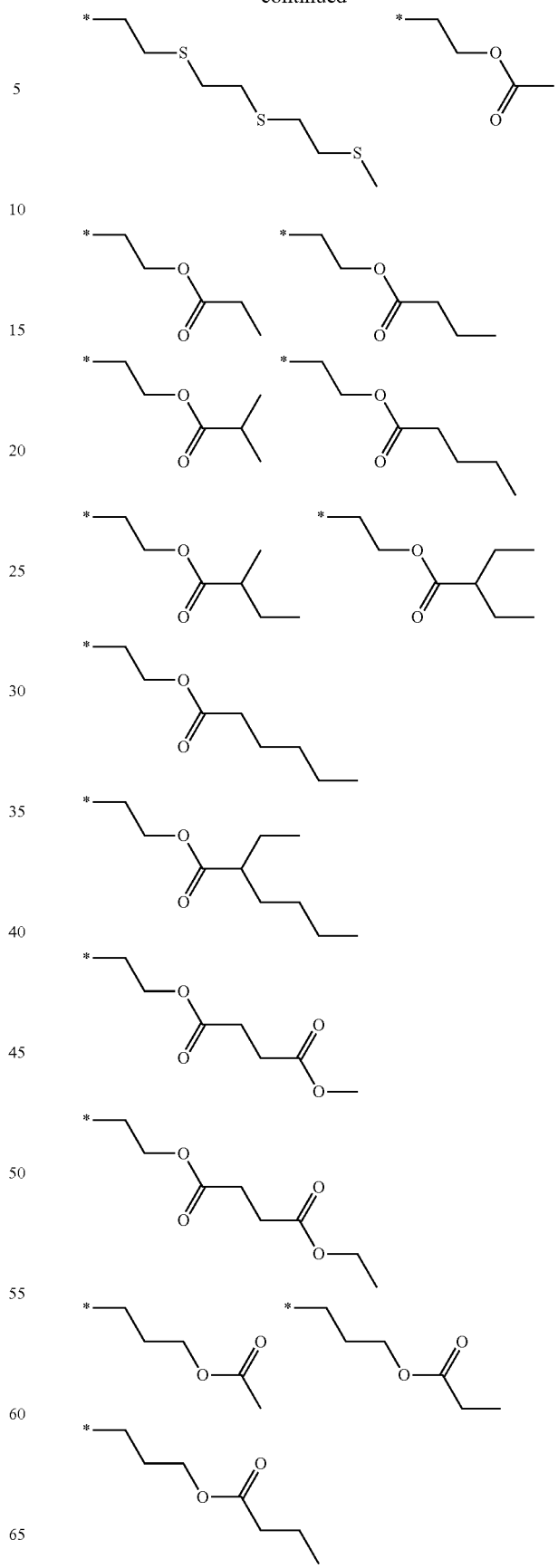

-continued

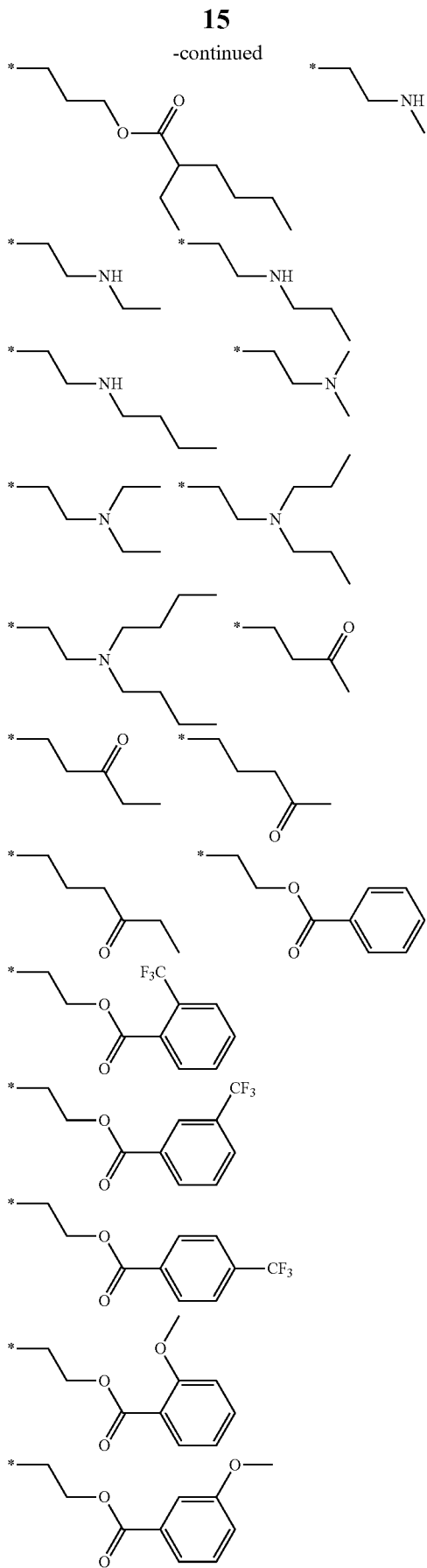

-continued

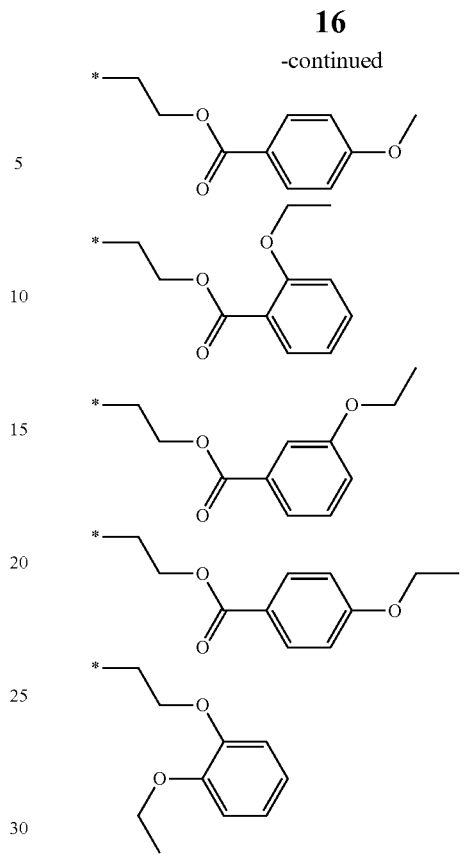

Examples of the halogen atom represented by $R^{11}$ and $R^{12}$ include a fluorine atom, a chlorine atom, a bromine atom and an iodine atom.

Examples of the alkyl halide group having 1 to 6 carbon atoms represented by $R^{11}$ and $R^{12}$ include alkyl fluoride groups, alkyl chloride groups, alkyl bromide groups and alkyl iodide groups having 1 to 6 carbon atoms.

Each of $R^1$ to $R^4$ is preferably a hydrogen atom, a hydroxy group and a methyl group, more preferably a hydrogen atom.

For $R^5$ to $R^8$, preferably, any one of $R^5$ and $R^6$ is a hydroxy group, and any one of $R^7$ and $R^8$ is a hydroxy group.

Each of $R^9$ and $R^{10}$ is preferably an alkyl group having 4 to 10 carbon atoms (wherein a hydrogen atom contained in the alkyl group is optionally replaced with a halogen atom or a phenyl group optionally having a substituent, and —$CH_2$— contained in the alkyl group is optionally replaced with —O—, —or —C(=O)—), more preferably an octyl group, a nonyl group, a decyl group, a dodecyl group, a 2-ethylhexyl group, or a group represented by any of the following formulas:

[Formula 10]

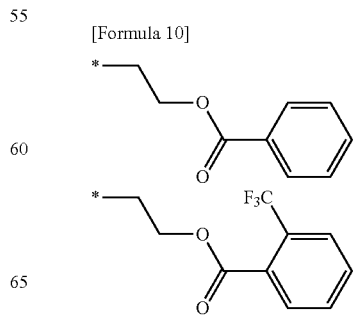

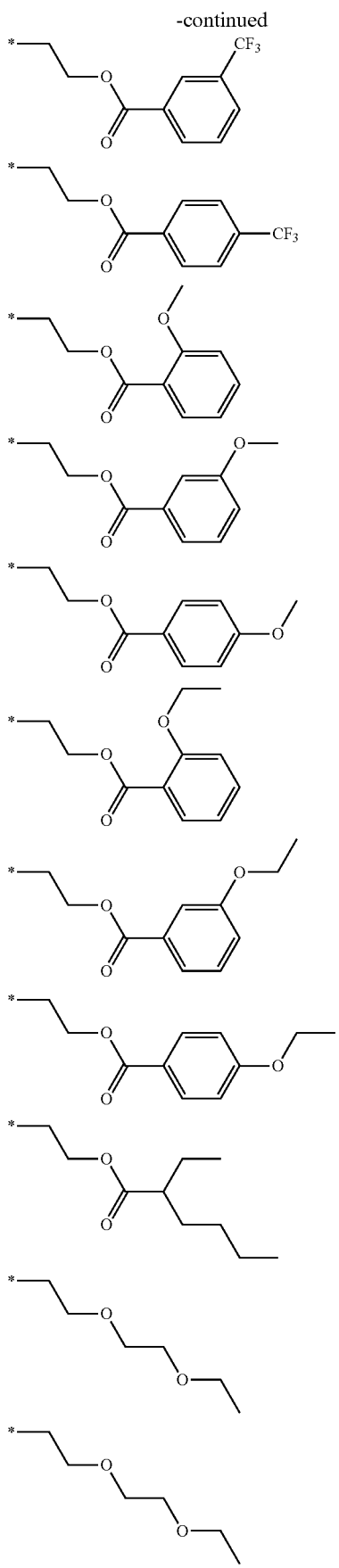
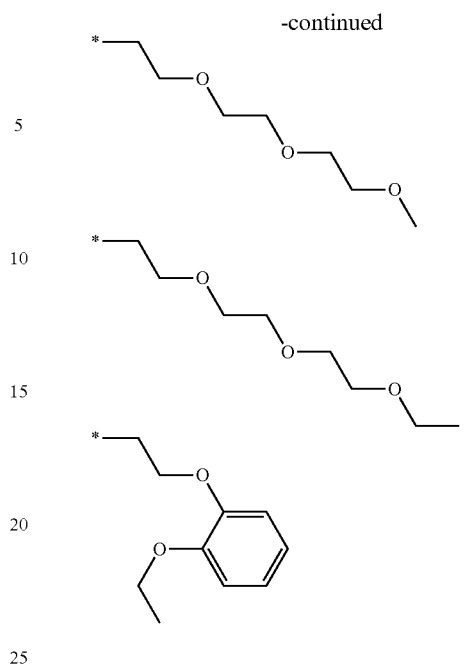
further preferably a 2-ethylhexyl group or a group represented by any of the following formulas:
[Formula 11]
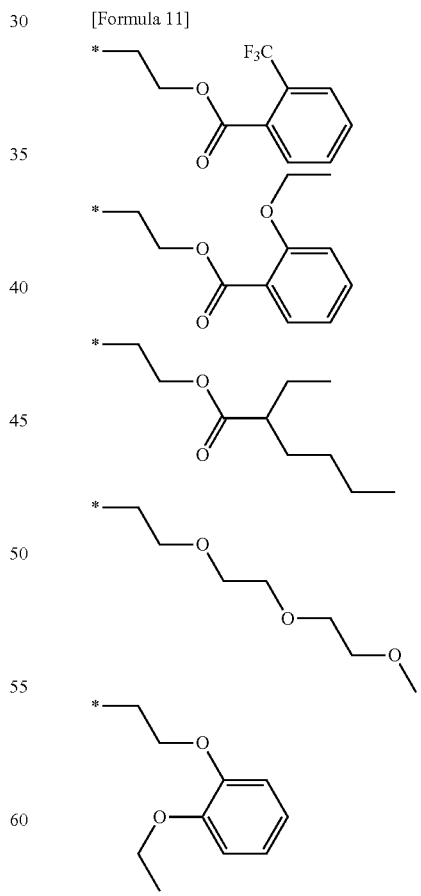
Each of $R^{11}$ and $R^{12}$ is preferably a fluorine atom or an alkyl fluoride group having 1 to 6 carbon atoms, more preferably a fluorine atom or a trifluoromethyl group.

In the formula (I), when a group represented by
[Formula 12]
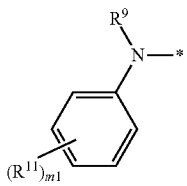
is defined as $X^1$, and a group represented by
[Formula 13]
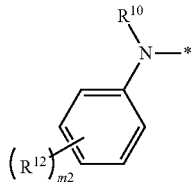
is defined as $X^2$, examples of the group represented by $X^1$ and $X^2$ include groups represented by the formulas (A2-1) to (A2-36) given below. * represents a bond to a carbon atom.
[Formula 14]
(A2-1)
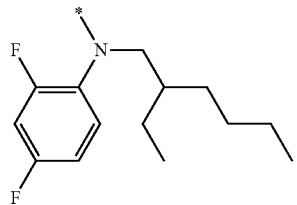
(A2-2)
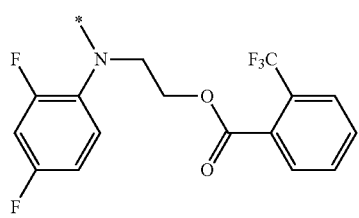
(A2-3)
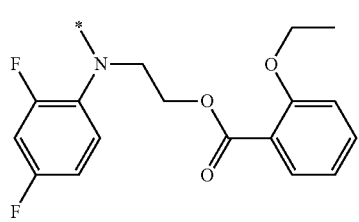
(A2-4)
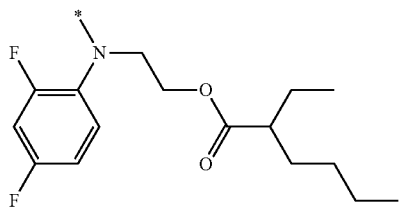
(A2-5)
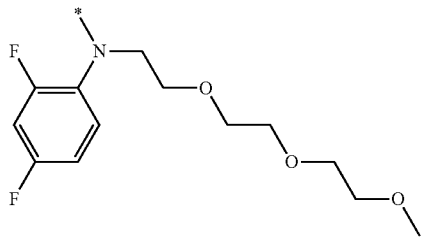
(A2-6)
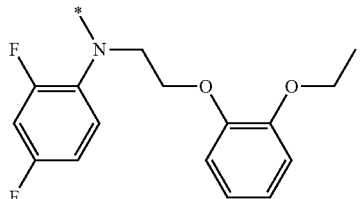
(A2-7)
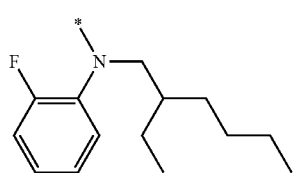
(A2-8)
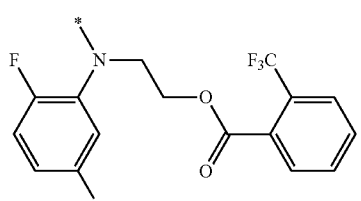
(A2-9)
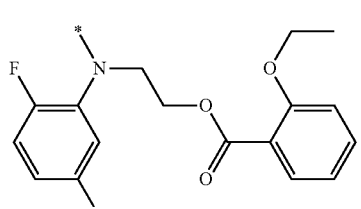
(A2-10)
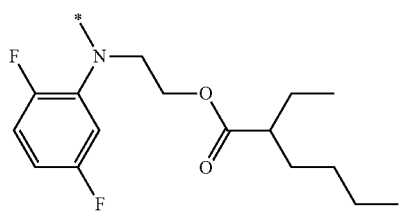

(A2-11) 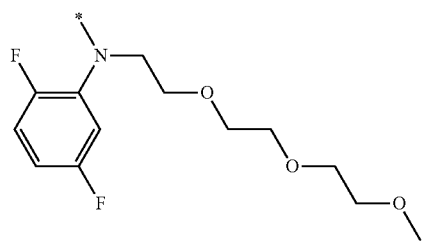
(A2-12) 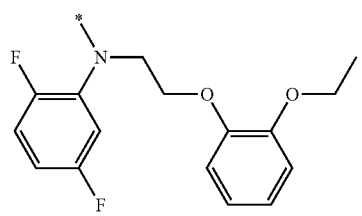
(A2-13) 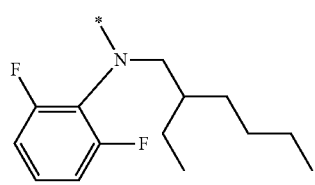
(A2-14) 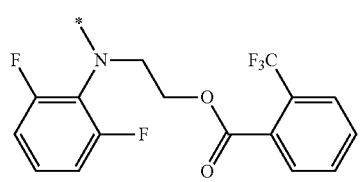
(A2-15) 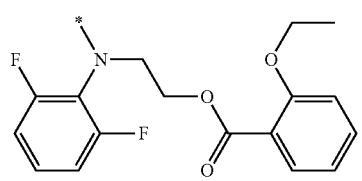
(A2-16) 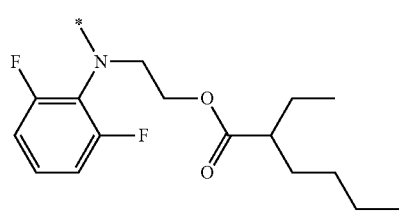
(A2-17) 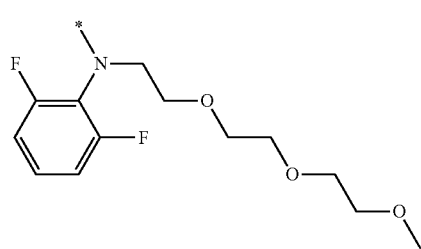
(A2-18) 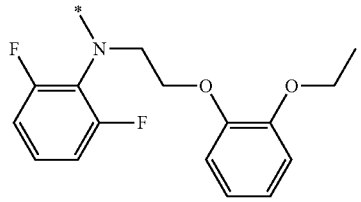
(A2-19) 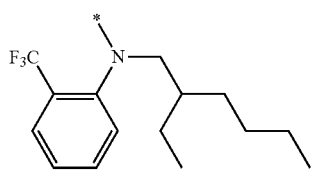
(A2-20) 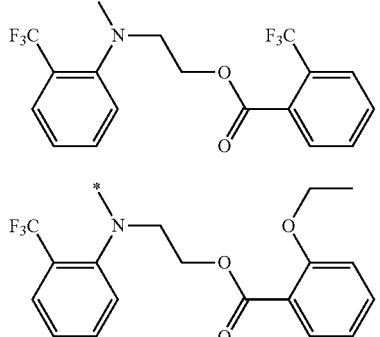
(A2-21) 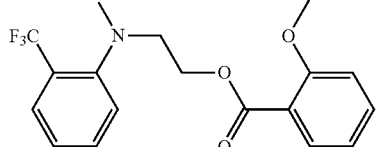
(A2-22) 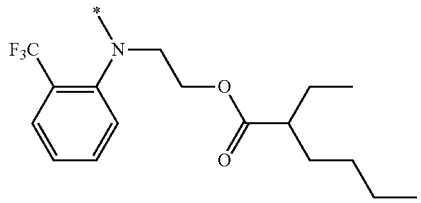
(A2-23) 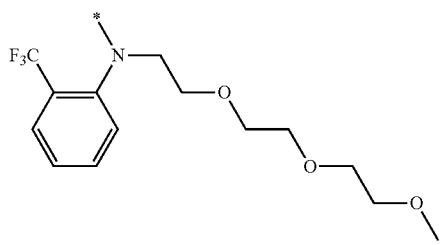
(A2-24) 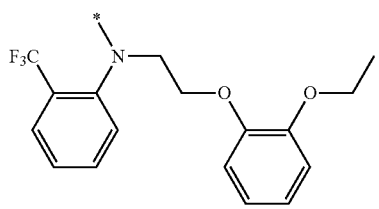
(A2-25) 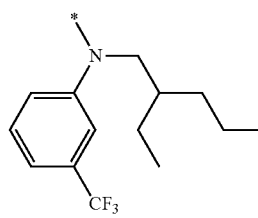

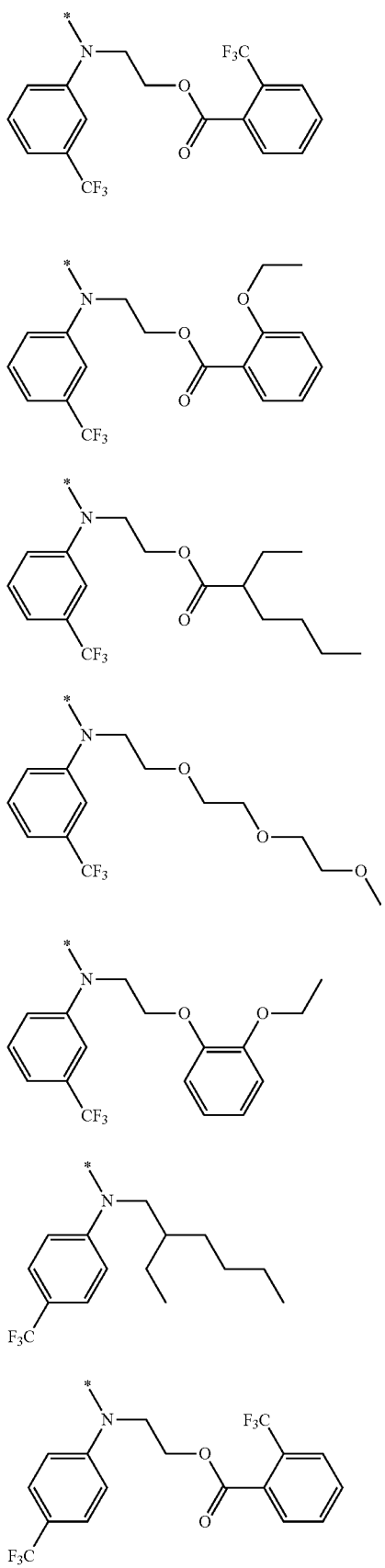
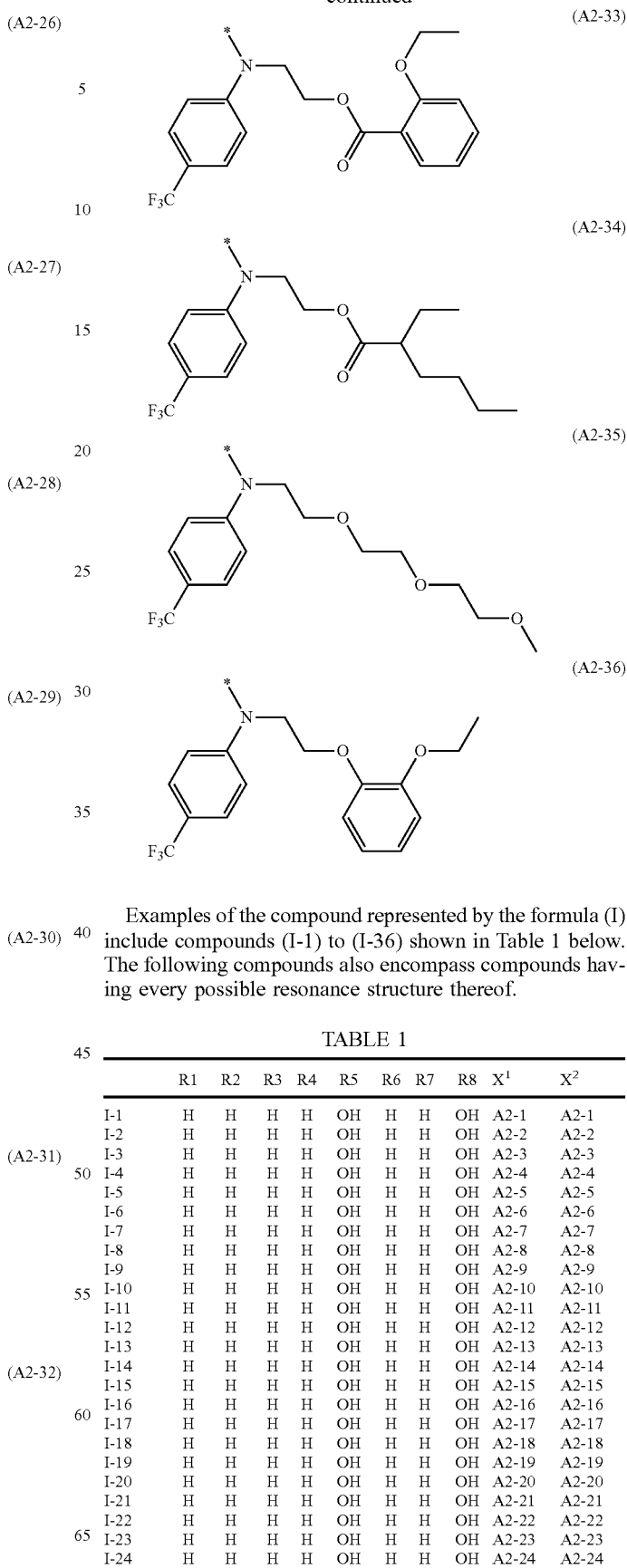

Examples of the compound represented by the formula (I) include compounds (I-1) to (I-36) shown in Table 1 below. The following compounds also encompass compounds having every possible resonance structure thereof.

TABLE 1

| | R1 | R2 | R3 | R4 | R5 | R6 | R7 | R8 | $X^1$ | $X^2$ |
|---|---|---|---|---|---|---|---|---|---|---|
| I-1 | H | H | H | H | OH | H | H | OH | A2-1 | A2-1 |
| I-2 | H | H | H | H | OH | H | H | OH | A2-2 | A2-2 |
| I-3 | H | H | H | H | OH | H | H | OH | A2-3 | A2-3 |
| I-4 | H | H | H | H | OH | H | H | OH | A2-4 | A2-4 |
| I-5 | H | H | H | H | OH | H | H | OH | A2-5 | A2-5 |
| I-6 | H | H | H | H | OH | H | H | OH | A2-6 | A2-6 |
| I-7 | H | H | H | H | OH | H | H | OH | A2-7 | A2-7 |
| I-8 | H | H | H | H | OH | H | H | OH | A2-8 | A2-8 |
| I-9 | H | H | H | H | OH | H | H | OH | A2-9 | A2-9 |
| I-10 | H | H | H | H | OH | H | H | OH | A2-10 | A2-10 |
| I-11 | H | H | H | H | OH | H | H | OH | A2-11 | A2-11 |
| I-12 | H | H | H | H | OH | H | H | OH | A2-12 | A2-12 |
| I-13 | H | H | H | H | OH | H | H | OH | A2-13 | A2-13 |
| I-14 | H | H | H | H | OH | H | H | OH | A2-14 | A2-14 |
| I-15 | H | H | H | H | OH | H | H | OH | A2-15 | A2-15 |
| I-16 | H | H | H | H | OH | H | H | OH | A2-16 | A2-16 |
| I-17 | H | H | H | H | OH | H | H | OH | A2-17 | A2-17 |
| I-18 | H | H | H | H | OH | H | H | OH | A2-18 | A2-18 |
| I-19 | H | H | H | H | OH | H | H | OH | A2-19 | A2-19 |
| I-20 | H | H | H | H | OH | H | H | OH | A2-20 | A2-20 |
| I-21 | H | H | H | H | OH | H | H | OH | A2-21 | A2-21 |
| I-22 | H | H | H | H | OH | H | H | OH | A2-22 | A2-22 |
| I-23 | H | H | H | H | OH | H | H | OH | A2-23 | A2-23 |
| I-24 | H | H | H | H | OH | H | H | OH | A2-24 | A2-24 |

TABLE 1-continued

| | R1 | R2 | R3 | R4 | R5 | R6 | R7 | R8 | X$^1$ | X$^2$ |
|---|---|---|---|---|---|---|---|---|---|---|
| I-25 | H | H | H | H | OH | H | H | OH | A2-25 | A2-25 |
| I-26 | H | H | H | H | OH | H | H | OH | A2-26 | A2-26 |
| I-27 | H | H | H | H | OH | H | H | OH | A2-27 | A2-27 |
| I-28 | H | H | H | H | OH | H | H | OH | A2-28 | A2-28 |
| I-29 | H | H | H | H | OH | H | H | OH | A2-29 | A2-29 |
| I-30 | H | H | H | H | OH | H | H | OH | A2-30 | A2-30 |
| I-31 | H | H | H | H | OH | H | H | OH | A2-31 | A2-31 |
| I-32 | H | H | H | H | OH | H | H | OH | A2-32 | A2-32 |
| I-33 | H | H | H | H | OH | H | H | OH | A2-33 | A2-33 |

TABLE 1-continued

| | R1 | R2 | R3 | R4 | R5 | R6 | R7 | R8 | X$^1$ | X$^2$ |
|---|---|---|---|---|---|---|---|---|---|---|
| I-34 | H | H | H | H | OH | H | H | OH | A2-34 | A2-34 |
| I-35 | H | H | H | H | OH | H | H | OH | A2-35 | A2-35 |
| I-36 | H | H | H | H | OH | H | H | OH | A2-36 | A2-36 |

Among them, compounds represented by the following formulas (I-1), (I-7), (I-13), (I-19), (I-25), and (I-31) are preferred from the viewpoint of starting material availability.

[Formula 15]

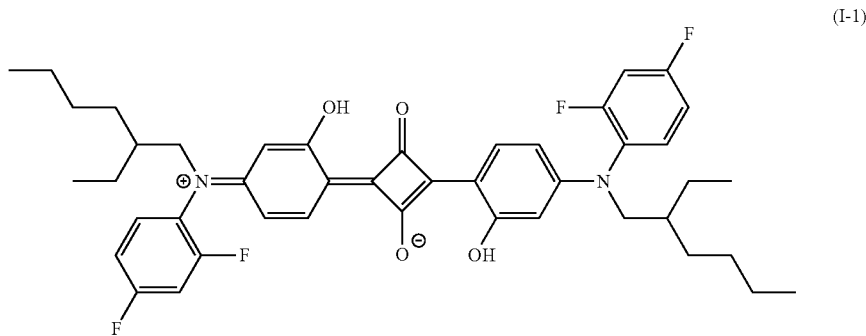

(I-1)

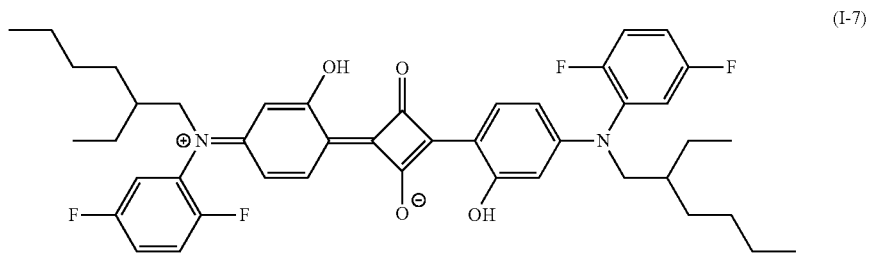

(I-7)

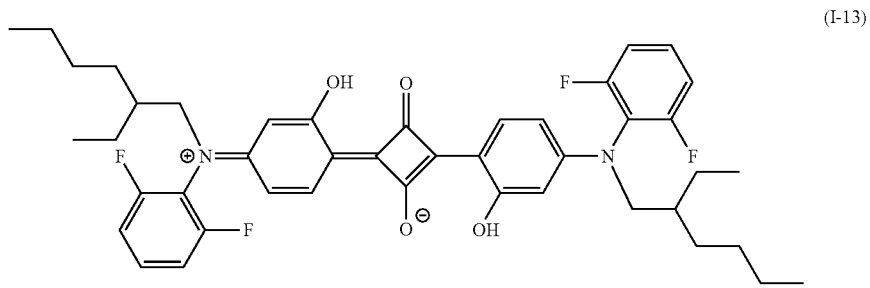

(I-13)

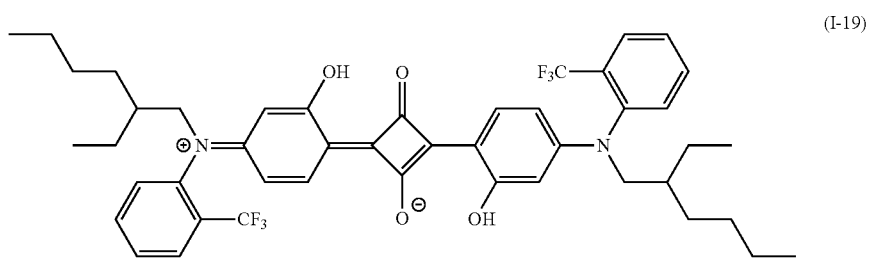

(I-19)

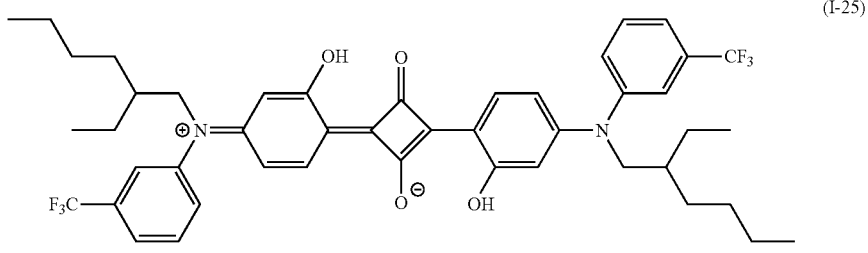

(I-25)

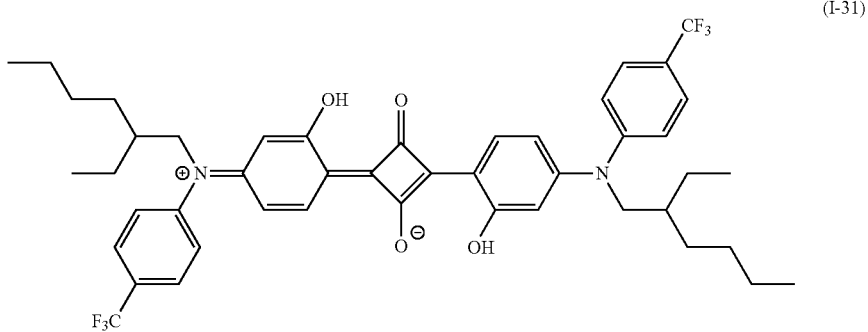

(I-31)

The compound (I) of the present invention can be produced by, for example, a method disclosed in Japanese Patent Laid-Open No. 2015-86379, a method comprising reacting a compound represented by the following formula (IV-1) with squaric acid (3,4-dihydroxy-3-cyclobutene-1,2-dione) (hereinafter, also referred to as method 1), or a method comprising reacting a compound represented by the following formula (IV-1) with 3,4-dihydroxy-3-cyclobutene-1,2-dione to obtain a compound represented by the following formula (V-1), and reacting the obtained compound of the following formula (V-1) with a compound represented by the following formula (IV-2) (hereinafter, also referred to as method 2):

[Formula 16]

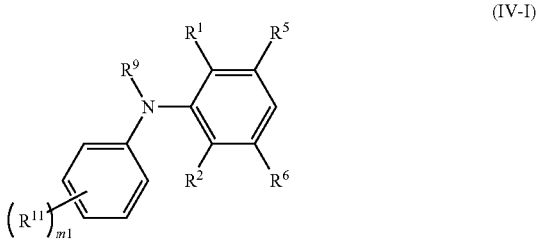

(IV-I)

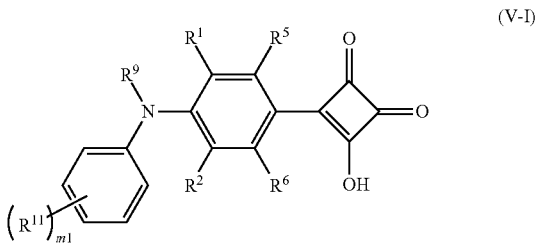

(V-I)

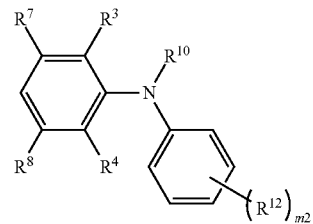

(IV-2)

wherein $R^1$ to $R^4$ each independently represent a hydrogen atom, a halogen atom, a hydroxy group or a monovalent saturated hydrocarbon group having 1 to 20 carbon atoms, wherein a hydrogen atom contained in the saturated hydrocarbon group is optionally replaced with a halogen atom, a hydroxy group or —N(R$^a$)$_2$, and —CH$_2$— contained in the saturated hydrocarbon group is optionally replaced with —O— or —S—; $R^a$ represents a hydrogen atom or an alkyl group having 1 to 8 carbon atoms;

$R^5$ to $R^8$ each independently represent a hydrogen atom or a hydroxy group;

$R^9$ and $R^{10}$ each independently represent a monovalent saturated hydrocarbon group having 1 to 20 carbon atoms, wherein a hydrogen atom contained in the saturated hydrocarbon group is optionally replaced with a halogen atom, a hydroxy group, —N(R$^b$)$_2$ or an aromatic hydrocarbon group having 6 to 20 carbon atoms and optionally having a substituent, and —CH$_2$— contained in the saturated hydrocarbon group is optionally replaced with —O—, —S—, —NR$^b$— or —C(=O)—; R$^b$ represents a hydrogen atom or an alkyl group having 1 to 8 carbon atoms;

$R^{11}$ and $R^{12}$ each independently represent a halogen atom or an alkyl halide group having 1 to 6 carbon atoms;

m1 and m2 each independently represent an integer of 1 to 5; and when m1 is 2 or larger, a plurality of $R^{11}$ are the same as or different from each other, and when m2 is 2 or larger, a plurality of $R^{12}$ are the same as or different from each other.

Examples of the compound represented by the formula (IV-1) include compounds represented by the following formulas (a-1-3), (a-7-3), (a-13-3), (a-19-3), (a-25-3), and (a-31-3):

[Formula 17]

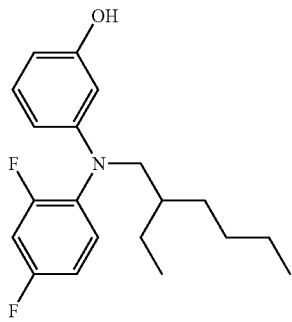
(a-1-3)

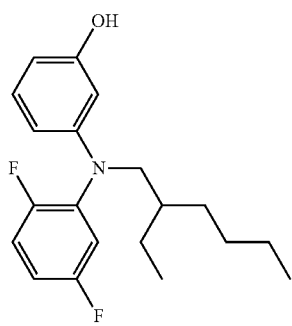
(a-7-3)

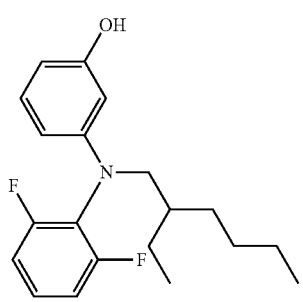
(a-13-3)

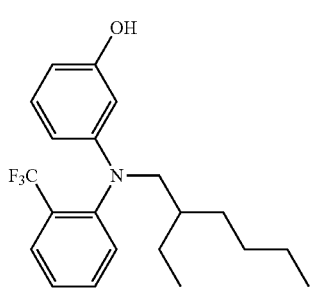
(a-19-3)

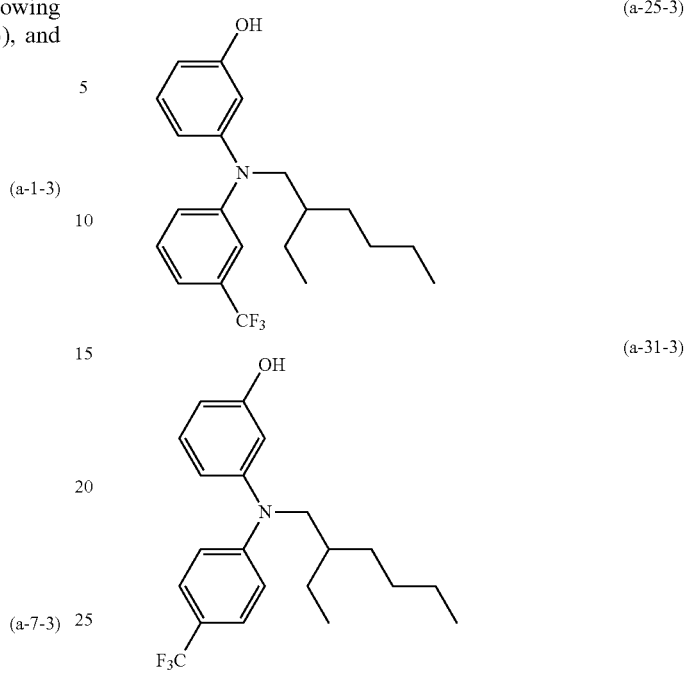

In the method 1, the amount of the squaric acid used is preferably 0.45 mol or more and 0.6 mol or less, more preferably 0.47 mol or more and 0.51 mol or less, per 1 mol of the compound represented by the formula (IV-I). In the method 2, the amount of the squaric acid used is preferably 0.9 mol or more and 1.2 mol or less, more preferably 0.94 mol or more and 1.02 mol or less, per 1 mol of the compound represented by the formula (IV-I).

The reaction temperature is preferably 30° C. to 180° C., more preferably 80° C. to 140° C. The reaction time is preferably 1 hour to 20 hours, more preferably 3 hours to 15 hours.

The reaction is preferably performed in an organic solvent from the viewpoint of a yield. Examples of the organic solvent include: hydrocarbon solvents such as toluene and xylene; halogenated hydrocarbon solvents such as chlorobenzene, dichlorobenzene, and chloroform; alcohol solvents such as methanol, ethanol, isopropanol, and butanol; nitro hydrocarbon solvents such as nitrobenzene; ketone solvents such as methyl isobutyl ketone; and amide solvents such as 1-methyl-2-pyrrolidone. A mixture of these solvents may be used. Among them, a mixed solvent of butanol and toluene is preferred. The amount of the organic solvent used is preferably 5 parts by mass or more and 50 parts by mass or less, more preferably 10 parts by mass or more and 30 parts by mass or less, per 1 part by mass of the compound represented by the formula (IV-I).

A method for obtaining the compound (I-1), which is the compound of interest, from the reaction mixture is not particularly limited, and various approaches known in the art can be adopted. Examples thereof can include a method comprising cooling the reaction mixture and then collecting precipitated crystals by filtration. The crystals thus collected by filtration are preferably washed with water or the like and subsequently dried. If necessary, the obtained compound may be further purified by an approach known in the art, such as recrystallization.

The compound represented by the formula (IV-1) can be produced by reacting a compound represented by the formula (IV-6) given below with boron tribromide. The compound represented by the formula (IV-6) given below can be produced by reacting a compound represented by the formula (IV-4) given below with a compound represented by the formula (IV-5) given below. The compound represented by the formula (IV-4) given below can be produced by reacting a compound represented by the formula (IV-2) given below with a compound represented by the formula (IV-3) given below.

[Formula 18]

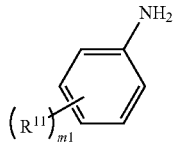

(IV-2)

wherein
each $R^{11}$ independently represents a halogen atom or an alkyl halide group having 1 to 6 carbon atoms;
each m1 independently represents an integer of 1 to 5; and when m1 is 2 or larger, a plurality of $R^{11}$ are the same as or different from each other.

[Formula 19]

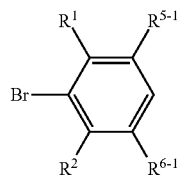

(IV-3)

wherein
$R^1$ and $R^2$ each independently represent a hydrogen atom, a halogen atom, a hydroxy group or a monovalent saturated hydrocarbon group having 1 to 20 carbon atoms, wherein a hydrogen atom contained in the saturated hydrocarbon group is optionally replaced with a halogen atom, a hydroxy group or —N($R^a$)$_2$, and —CH$_2$— contained in the saturated hydrocarbon group is optionally replaced with —O— or —S—; $R^a$ represents a hydrogen atom or an alkyl group having 1 to 8 carbon atoms; and
$R^{5-1}$ and $R^{6-1}$ each independently represent a hydrogen atom, a hydroxy group or an alkoxy group having 1 to 20 carbon atoms, and at least one of $R^{5-1}$ and $R^{6-1}$ represents a hydroxy group or an alkoxy group having 1 to 20 carbon atoms.

[Formula 20]

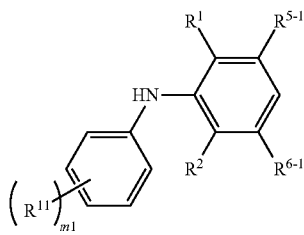

(IV-4)

wherein
$R^1$ and $R^2$ each independently represent a hydrogen atom, a halogen atom, a hydroxy group or a monovalent saturated hydrocarbon group having 1 to 20 carbon atoms, wherein a hydrogen atom contained in the saturated hydrocarbon group is optionally replaced with a halogen atom, a hydroxy group or —N($R^a$)$_2$, and —CH$_2$— contained in the saturated hydrocarbon group is optionally replaced with —O— or —S—; $R^a$ represents a hydrogen atom or an alkyl group having 1 to 8 carbon atoms;
$R^{5-1}$ and $R^{6-1}$ each independently represent a hydrogen atom, a hydroxy group or an alkoxy group having 1 to 20 carbon atoms, and at least one of $R^{5-1}$ and $R^{6-1}$ represents a hydroxy group or an alkoxy group having 1 to 20 carbon atoms;
each $R^{11}$ independently represents a halogen atom or an alkyl halide group having 1 to 6 carbon atoms;
each m1 independently represents an integer of 1 to 5; and when m1 is 2 or larger, a plurality of $R^{11}$ are the same as or different from each other.

[Formula 21]

(IV-5)

wherein
each $R^9$ independently represents a monovalent saturated hydrocarbon group having 1 to 20 carbon atoms, wherein a hydrogen atom contained in the saturated hydrocarbon group is optionally replaced with a halogen atom, a hydroxy group, —N($R^b$)$_2$ or an aromatic hydrocarbon group having 6 to 20 carbon atoms and optionally having a substituent, and —CH$_2$— contained in the saturated hydrocarbon group is optionally replaced with —O—, —S—, —NR$^b$— or —C(=O)—; and $R^b$ represents a hydrogen atom or an alkyl group having 1 to 8 carbon atoms.

[Formula 22]

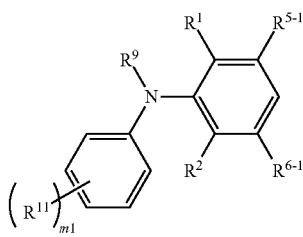

(IV-6)

wherein
$R^1$ and $R^2$ each independently represent a hydrogen atom, a halogen atom, a hydroxy group or a monovalent saturated hydrocarbon group having 1 to 20 carbon atoms, wherein a hydrogen atom contained in the saturated hydrocarbon group is optionally replaced with a halogen atom, a hydroxy group or —N($R^a$)$_2$, and —CH$_2$— contained in the saturated hydrocarbon group is optionally replaced with —O— or —S—; $R^a$ represents a hydrogen atom or an alkyl group having 1 to 8 carbon atoms;
$R^{5-1}$ and $R^{6-1}$ each independently represent a hydrogen atom, a hydroxy group or an alkoxy group having 1 to 20 carbon atoms, and at least one of $R^{5-1}$ and $R^{6-1}$ represents a hydroxy group or an alkoxy group having 1 to 20 carbon atoms;

each $R^9$ independently represents a monovalent saturated hydrocarbon group having 1 to 20 carbon atoms, wherein a hydrogen atom contained in the saturated hydrocarbon group is optionally replaced with a halogen atom, a hydroxy group, $-N(R^b)_2$ or an aromatic hydrocarbon group having 6 to 20 carbon atoms and optionally having a substituent, and $-CH_2-$ contained in the saturated hydrocarbon group is optionally replaced with $-O-$, $-S-$, $-NR^b-$ or $-C(=O)-$; $R^b$ represents a hydrogen atom or an alkyl group having 1 to 8 carbon atoms;

each $R^{11}$ independently represents a halogen atom or an alkyl halide group having 1 to 6 carbon atoms;

each m1 independently represents an integer of 1 to 5; and when m1 is 2 or larger, a plurality of $R^{11}$ are the same as or different from each other.

Examples of the compound represented by the formula (IV-2) include 2,4-difluoroaniline, 2,5-difluoroaniline, 2,6-difluoroaniline, 2-trifluoromethylaniline, 3-trifluoromethylaniline, and 4-trifluoromethylaniline represented by the following formulas:

[Formula 23]

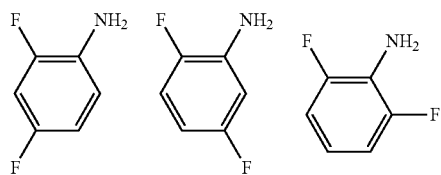

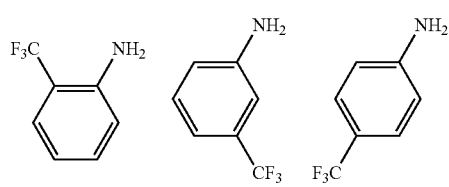

Examples of the compound represented by the formula (IV-3) include 3-bromoanisole represented by the following formula:

[Formula 24]

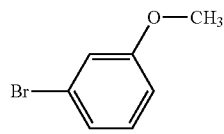

Examples of the compound represented by the formula (IV-4) include compounds represented by the following formulas (a-1-1), (a-7-1), (a-13-1), (a-19-1), (a-25-1), and (a-31-1):

[Formula 25]

(a-1-1)

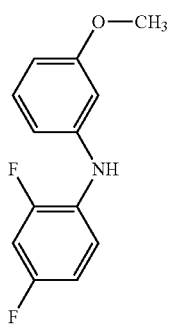

(a-7-1)

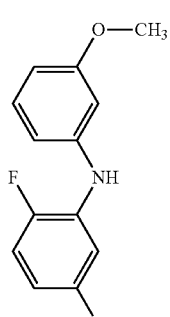

(a-13-1)

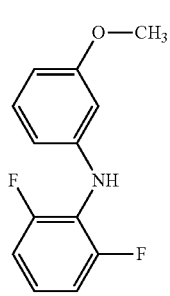

(a-19-1)

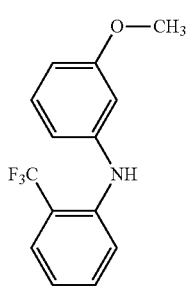

(a-25-1)

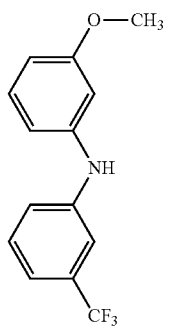

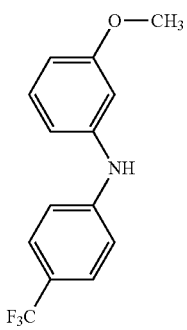
(a-31-1)

Examples of the compound represented by the formula (IV-5) include compounds represented by the following formula:

[Formula 26]

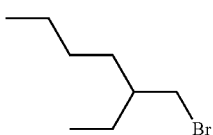

Examples of the compound represented by the formula (IV-6) include compounds represented by the following formulas (a-1-2), (a-7-2), (a-13-2), (a-19-2), (a-25-2), and (a-31-2):

[Formula 27]

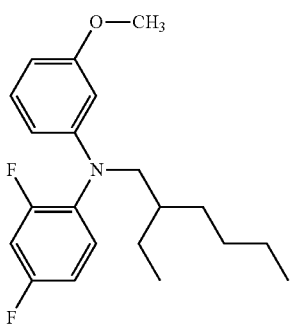
(a-1-2)

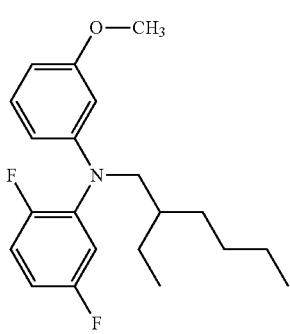
(a-7-2)

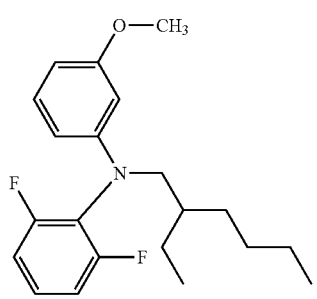
(a-13-2)

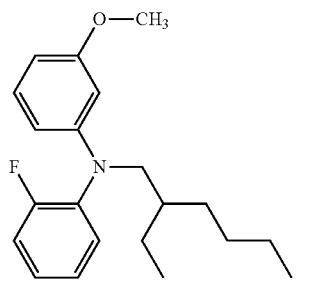
(a-19-2)

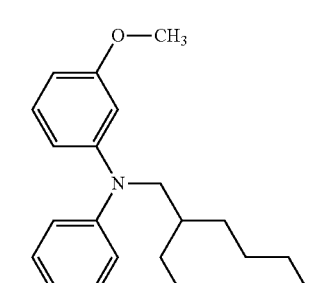
(a-25-2)

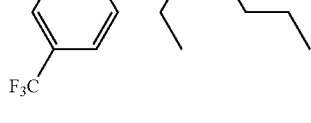
(a-31-2)

Examples of the method for producing the compound represented by the formula (IV-4) from the compound represented by the formula (IV-2) and the compound represented by the formula (IV-3) include various methods known in the art, for example, a method disclosed in J. Polymer Science Part A: Polymer Chemistry 2012, 50, 3788-3796 and a method disclosed in Japanese Patent Laid-Open No. 2016-11419 ([0140] and [0150]).

Examples of the method for producing the compound represented by the formula (IV-6) from the compound represented by the formula (IV-4) and the compound represented by the formula (IV-5) include various methods known in the art, for example, a method disclosed in Japanese Patent Laid-Open No. 2016-11419 ([0130]).

Examples of the method for producing the compound represented by the formula (IV-1) from the compound represented by the formula (IV-6) and boron tribromide include various methods known in the art, for example, a method disclosed in Japanese Patent Laid-Open No. 2016-11419 ([0132], [0152]).

<Colored Resin Composition>

The colored resin composition of the present invention comprises a colorant (A) comprising the compound of the present invention, and a resin (B). In the present specification, compounds listed as examples of each component can be used singly or in combinations of two or more thereof, unless otherwise specified.

<Colorant (A)>

The colorant (A) may comprise an additional dye as a dye (A-1), in addition to the compound (I). Examples of such a dye include dyes such as oil-soluble dyes, acid dyes, amine salts of acid dyes, and sulfonamide derivatives of acid dyes, and include compounds classified into dyes of solvent, acid, basic, reactive, direct, disperse, mordant, and vat types according to Color Index (published by The Society of Dyers and Colourists), and dyes known in the art disclosed in Dyeing Note (Shikisensha Co., Ltd.). Depending on chemical structures, examples of the dye include azo dyes, anthraquinone dyes, triphenylmethane dyes, xanthene dyes and phthalocyanine dyes. These dyes may be used singly or in combinations of two or more thereof.

Specific examples thereof include

C.I. Solvent dyes such as C.I. Solvent Yellow 4 (hereinafter, the term "C.I. Solvent Yellow" will be omitted, and only numbers will be described), 14, 15, 23, 24, 25, 38, 62, 63, 68, 79, 81, 82, 83, 89, 94, 98, 99, and 162;

C.I. Solvent Orange 2, 7, 11, 15, 26, and 56;

C.I. Solvent Red 24, 49, 90, 91, 111, 118, 119, 122, 124, 125, 127, 130, 132, 143, 145, 146, 150, 151, 155, 160, 168, 169, 172, 175, 181, 207, 218, 222, 227, 230, 245, and 247;

C.I. Solvent Violet 11, 13, 14, 26, 31, 36, 37, 38, 45, 47, 48, 51, 59, and 60;

C.I. Solvent Blue 14, 18, 35, 36, 45, 58, 59, 59:1, 63, 68, 69, 78, 79, 83, 94, 97, 98, 100, 101, 102, 104, 105, 111, 112, 122, 128, 132, 136, and 139; and C.I. Solvent Green 1, 3, 5, 28, 29, 32, and 33, C.I. Acid dyes such as C.I. Acid Yellow 1, 3, 7, 9, 11, 17, 23, 25, 29, 34, 36, 38, 40, 42, 54, 65, 72, 73, 76, 79, 98, 99, 111, 112, 113, 114, 116, 119, 123, 128, 134, 135, 138, 139, 140, 144, 150, 155, 157, 160, 161, 163, 168, 169, 172, 177, 178, 179, 184, 190, 193, 196, 197, 199, 202, 203, 204, 205, 207, 212, 214, 220, 221, 228, 230, 232, 235, 238, 240, 242, 243, and 251;

C.I. Acid Orange 6, 7, 8, 10, 12, 26, 50, 51, 52, 56, 62, 63, 64, 74, 75, 94, 95, 107, 108, 149, 162, 169, and 173;

C.I. Acid Red 73, 80, 91, 92, 97, 138, 151, 211,274, and 289;

C.I. Acid Green 3, 5, 9, 25, 27, 28, and 41;

C.I. Acid Violet 34 and 120; and

C.I. Acid Blue 25, 27, 40, 45, 78, 80, and 112,

C.I. Basic dyes such as C.I. Basic Green 1,

C.I. Reactive dyes such as C.I. Reactive Yellow 2, 76, and 116; and

C.I. Reactive Orange 16,

C.I. Direct dyes such as C.I. Direct Yellow 2, 4, 28, 33, 34, 35, 38, 39, 43, 44, 47, 50, 54, 58, 68, 69, 70, 71, 86, 93, 94, 95, 98, 102, 108, 109, 129, 132, 136, 138, and 141;

C.I. Direct Orange 26, 34, 39, 41, 46, 50, 52, 56, 57, 61, 64, 65, 68, 70, 96, 97, 106, and 107; and C.I. Direct Blue 40, C.I. Disperse dyes such as C.I. Disperse Yellow 51, 54, and 76;

C.I. Disperse Violet 26 and 27; and

C.I. Disperse Blue 1, 14, 56, and 60,

C.I. Mordant dyes such as C.I. Mordant Yellow 5, 8, 10, 16, 20, 26, 30, 31, 33, 42, 43, 45, 56, 61, 62, and 65; and C.I. Mordant Orange 3, 4, 5, 8, 12, 13, 14, 20, 21, 23, 24, 28, 29, 32, 34, 35, 36, 37, 42, 43, 47, and 48, and C.I. Vat dyes such as C.I. Vat Green 1.

The content of the compound (I) in the dye (A-1) is preferably 3% by mass or more and 100% by mass or less, more preferably 10% by mass or more and 70% by mass or less, further preferably 15% by mass or more and 50% by mass or less, based on the total amount of the dye (A-1). When the content of the compound (I) falls within the range described above, the resulting color filter tends to obtain high color reproducibility and be easily thinned.

The colorant (A) preferably comprises a pigment (A-2). The pigment (A-2) is not particularly limited, and a pigment known in the art can be used. Examples thereof include pigments classified into pigment type according to Color Index (published by The Society of Dyers and Colourists). These pigments can be used singly or in combinations of two or more thereof.

Examples of the pigment (A-2) include:

yellow pigments such as C.I. Pigment Yellow 1, 3, 12, 13, 14, 15, 16, 17, 20, 24, 31, 53, 83, 86, 93, 94, 109, 110, 117, 125, 128, 129, 137, 138, 139, 147, 148, 150, 153, 154, 166, 173, 194, and 214;

orange pigments such as C.I. Pigment Orange 13, 31, 36, 38, 40, 42, 43, 51, 55, 59, 61, 64, 65, 71, and 73;

red pigments such as C.I. Pigment Red 9, 97, 105, 122, 123, 144, 149, 166, 168, 176, 177, 180, 192, 209, 215, 216, 224, 242, 254, 255, 264, and 265;

blue pigments such as C.I. Pigment Blue 15, 15:3, 15:4, 15:6, and 60;

violet pigments such as C.I. Pigment Violet 1, 19, 23, 29, 32, 36, and 38;

green pigments such as C.I. Pigment Green 7, 36, and 58;

brown pigments such as C.I. Pigment Brown 23 and 25; and black pigments such as C.I. Pigment Black 1 and 7.

The pigment (A-2) is preferably a yellow pigment such as C.I. Pigment Yellow 1, 3, 12, 13, 14, 15, 16, 17, 20, 24, 31, 53, 83, 86, 93, 94, 109, 110, 117, 125, 128, 137, 138, 139, 147, 148, 150, 153, 154, 166, 173, 185, 194, or 214; or a green pigment such as C.I. Pigment Green 7, 36, or 58, more preferably C.I. Pigment Yellow 138, 150, or 185 or C.I. Pigment Green 58, further preferably C.I. Pigment Yellow 138 or C.I. Pigment Green 58. When the pigment is contained therein, transmission spectra are easily optimized. Thus, the resulting color filter has favorable light resistance and chemical resistance.

If necessary, the pigment may be subjected to, for example, rosin treatment, surface treatment using a pigment derivative or the like with an acidic group or a basic group introduced therein, graft treatment of pigment surface with a polymer compound or the like, atomization treatment by a sulfuric acid atomization method or the like, or washing treatment with an organic solvent, water or the like or removal treatment by an ion-exchange method or the like of ionic impurities in order to remove impurities.

The pigment preferably has a uniform particle size. A pigment dispersion in a state where the pigment is uniformly dispersed in a solution can be obtained by dispersion treatment with a pigment dispersant contained therein.

Examples of the pigment dispersant include surfactants. Any of cationic, anionic, and amphoteric surfactants can be used. Specific examples thereof include polyester, polyamine, and acrylic surfactants. These pigment dispersants may be used singly or in combinations of two or more thereof. Examples of the pigment dispersant in terms of trade name include KP (manufactured by Shin-Etsu Chemical Co., Ltd.), Flowlen (manufactured by Kyoeisha Chemical Co., Ltd.), Solsperse(R) (manufactured by AstraZeneca K.K.), EFKA(R) (manufactured by BASF SE), Ajisper(R) (manufactured by Ajinomoto Fine-Techno Co., Inc.), and Disperbyk(R) (manufactured by BYK Japan K.K.).

In the case of using a pigment dispersant, the amount of the pigment dispersant used is preferably 1% by mass or more and 100% by mass or less, more preferably 5% by mass or more and 50% by mass or less, based on the total amount of the pigment (A-2). When the amount of the pigment dispersant used falls within the range described above, a pigment dispersion in a uniformly dispersed state tends to be obtained.

In the colorant (A) comprising the pigment (A-2), the content ratio between the dye (A-1) and the pigment (A-2) is usually 45:55 to 1:99, preferably 40:60 to 2:98, more preferably 38:62 to 3:97, based on mass.

The content of the colorant (A) is preferably 5% by mass or more and 60% by mass or less, more preferably 8% by mass or more and 55% by mass or less, further preferably 10% by mass or more and 50% by mass or less, based on the total amount of solid components. When the content of the colorant (A) falls within the range described above, the resulting color filter has a sufficient color density and tends to be able to be easily thinned because the composition can contain a necessary amount of the resin (B) or a polymerizable compound (C). In the present specification, the "total amount of solid components" refers to the total amount of the colored resin composition excluding the content of a solvent. The total amount of solid components and the content of each component based on this total amount can be measured by, for example, an analysis approach known in the art such as liquid chromatography or gas chromatography.

<Resin (B)>

The resin (B) is not particularly limited and is preferably an alkali-soluble resin. Examples of the resin (B) include the following resins [K1] to [K6]:

resin [K1]; a copolymer of (Ba) at least one member selected from the group consisting of an unsaturated carboxylic acid and an unsaturated carboxylic anhydride (hereinafter, also referred to as "(Ba)") and (Bb) a monomer having a cyclic ether structure having 2 to 4 carbon atoms and an ethylenic unsaturated bond (hereinafter, also referred to as "(Bb)");

resin [K2]; a copolymer of (Ba), (Bb), and (Bc) a monomer copolymerizable with (Ba) (provided that the monomer (Bc) is different from (Ba) and (Bb)) (hereinafter, also referred to as"(Bc)");

resin [K3]; a copolymer of (Ba) and (Bc);

resin [K4]; a resin obtained by reacting a copolymer of (Ba) and (Bc) with (Bb);

resin [K5]; a resin obtained by reacting a copolymer of (Bb) and (Bc) with (Ba); and resin [K6]; a resin obtained by reacting a copolymer of (Bb) and (Bc) with (Ba) and further with a carboxylic anhydride.

Specific examples of (Ba) include:

unsaturated monocarboxylic acids such as acrylic acid, methacrylic acid, crotonic acid, and o-, m-, and p-vinylbenzoic acids;

unsaturated dicarboxylic acids such as maleic acid, fumaric acid, citraconic acid, mesaconic acid, itaconic acid, 3-vinylphthalic acid, 4-vinylphthalic acid, 3,4,5,6-tetrahydrophthalic acid, 1,2,3,6-tetrahydrophthalic acid, dimethyltetrahydrophthalic acid, and 1, 4-cyclohexenedicarboxylic acid;

bicyclo unsaturated compounds containing a carboxy group, such as methyl-5-norbornene-2,3-dicarboxylic acid, 5-carboxybicyclo[2.2.1]hept-2-ene, 5,6-dicarboxybicyclo[2.2.1]hept-2-ene, 5-carboxy-5-methylbicyclo[2.2.1]hept-2-ene, 5-carboxy-5-ethylbicyclo[2.2.1]hept-2-ene, 5-carboxy-6-methylbicyclo[2.2.1]hept-2-ene, and 5-carboxy-6-ethylbicyclo[2.2.1]hept-2-ene;

unsaturated dicarboxylic anhydrides such as maleic anhydride, citraconic anhydride, itaconic anhydride, 3-vinylphthalic anhydride, 4-vinylphthalic anhydride, 3,4,5,6-tetrahydrophthalic anhydride, 1,2,3,6-tetrahydrophthalic anhydride, dimethyltetrahydrophthalic anhydride, and 5,6-dicarboxybicyclo[2.2.1]hept-2-ene anhydride;

unsaturated mono[(meth)acryloyloxyalkyl] esters of divalent or higher polyvalent carboxylic acids, such as mono[2-(meth)acryloyloxyethyl] succinate and mono[2-(meth)acryloyloxyethyl] phthalate; and unsaturated acrylates containing a hydroxy group and a carboxy group in the same molecule, such as α-(hydroxymethyl)acrylic acid.

Among them, acrylic acid, methacrylic acid, maleic anhydride, or the like is preferred from the viewpoint of copolymerization reactivity or from the viewpoint of the solubility of the resulting resin in an aqueous alkali solution.

(Bb) refers to, for example, a polymerizable compound having a cyclic ether structure having 2 to 4 carbon atoms (e.g., at least one member selected from the group consisting of an oxirane ring, an oxetane ring and a tetrahydrofuran ring) and an ethylenic unsaturated bond. (Bb) is preferably a monomer having a cyclic ether having 2 to 4 carbon atoms and a (meth)acryloyloxy group.

In the present specification, the "(meth)acrylic acid" represents at least one member selected from the group consisting of acrylic acid and methacrylic acid. Terms such as "(meth)acryloyl" and "(meth)acrylate" also have similar meanings.

Examples of (Bb) include monomers having an oxiranyl group and an ethylenic unsaturated bond, monomers having an oxetanyl group and an ethylenic unsaturated bond, and monomers having a tetrahydrofuryl group and an ethylenic unsaturated bond.

(Bb) is preferably a monomer having an oxiranyl group and an ethylenic unsaturated bond from the viewpoint that the resulting color filter can have higher reliability such as heat resistance and chemical resistance.

Examples of (Bc) include:

(meth)acrylic acid esters such as methyl (meth)acrylate, ethyl (meth)acrylate, n-butyl (meth)acrylate, sec-butyl (meth)acrylate, tert-butyl (meth)acrylate, 2-ethylhexyl (meth)acrylate, dodecyl (meth)acrylate, lauryl (meth)acrylate, stearyl (meth)acrylate, cyclopentyl (meth)acrylate, cyclohexyl (meth)acrylate, 2-methylcyclohexyl (meth)acrylate, tricyclo[5.2.1.0$^{2,6}$]decan-8-yl (meth)acrylate (referred to as "dicyclopentanyl (meth)acrylate" as a trivial name in the art; also referred to as "tricyclodecyl (meth)acrylate"), tricyclo[5.2.1.0$^{2,6}$]decan-8-yl (meth)acrylate (referred to as "dicyclopentenyl (meth)acrylate" as a trivial name in the art), dicyclopentanyloxyethyl (meth)acrylate, isobornyl (meth)acrylate, adamantyl (meth)acrylate, allyl (meth)acrylate, propargyl (meth)acrylate, phenyl (meth)acrylate, naphthyl (meth)acrylate, and benzyl (meth)acrylate;

hydroxy group-containing (meth)acrylic acid esters such as 2-hydroxyethyl (meth)acrylate and 2-hydroxypropyl (meth)acrylate;

dicarboxylic acid diesters such as diethyl maleate, diethyl fumarate, and diethyl itaconate;

bicyclo unsaturated compounds such as bicyclo[2.2.1]hept-2-ene, 5-methylbicyclo[2.2.1]hept-2-ene, 5-ethylbicyclo[2.2.1]hept-2-ene, 5-hydroxybicyclo[2.2.1]hept-2-ene, 5-hydroxymethylbicyclo[2.2.1]hept-2-ene, 5-(2'-hydroxyethyl)bicyclo[2.2.1]hept-2-ene, 5-methoxybicyclo[2.2.1]hept-2-ene, 5-ethoxybicyclo[2.2.1]hept-2-ene, 5,6-dihydroxybicyclo[2.2.1]hept-2-ene, 5,6-di(hydroxymethyl)bicyclo[2.2.1]hept-2-ene, 5,6-di(2'-hydroxyethyl)bicyclo[2.2.1]hept-2-ene, 5,6-dimethoxybicyclo[2.2.1]hept-2-ene, 5,6-diethoxybicyclo[2.2.1]hept-2-ene, 5-hydroxy-5-methylbicyclo[2.2.1]hept-2-ene, 5-hydroxy-5-ethylbicyclo[2.2.1]hept-2-ene, 5-hydroxymethyl-5-methylbicyclo[2.2.1]hept-2-ene, 5-tert-butoxycarbonylbicyclo[2.2.1]hept-2-ene, 5-cyclohexyloxycarbonylbicyclo[2.2.1]hept-2-ene, 5-phenoxycarbonylbicyclo[2.2.1]hept-2-ene, 5,6-bis(tert-butoxycarbonyl)bicyclo[2.2.1]hept-2-ene, and 5,6-bis(cyclohexyloxycarbonyl)bicyclo[2.2.1]hept-2-ene;

dicarbonylimide derivatives such as N-phenylmaleimide, N-cyclohexylmaleimide, N-benzylmaleimide, N-succinimidyl-3-maleimide benzoate, N-succinimidyl-4-maleimide butyrate, N-succinimidyl-6-maleimide caproate, N-succinimidyl-3-maleimide propionate, and N-(9-acridinyl)maleimide; and styrene, α-methylstyrene, m-methylstyrene, p-methylstyrene, vinyltoluene, p-methoxystyrene, acrylonitrile, methacrylonitrile, vinyl chloride, vinylidene chloride, acrylamide, methacrylamide, vinyl acetate, 1,3-butadiene, isoprene, and 2,3-dimethyl-1,3-butadiene.

Among them, styrene, vinyltoluene, N-phenylmaleimide, N-cyclohexylmaleimide, N-benzylmaleimide, bicyclo[2.2.1]hept-2-ene, or the like is preferred from the viewpoint of copolymerization reactivity and heat resistance.

Specific examples of the resin (B) include: resins [K1] such as 3,4-epoxycyclohexylmethyl (meth)acrylate/(meth)acrylic acid copolymers and 3,4-epoxytricyclo[5.2.1.0$^{2.6}$]decyl acrylate/(meth)acrylic acid copolymers; resins [K2] such as glycidyl (meth)acrylate/benzyl (meth)acrylate/(meth)acrylic acid copolymers, glycidyl (meth)acrylate/styrene/(meth)acrylic acid copolymers, 3,4-epoxytricyclo[5.2.1.0$^{2.6}$]decyl acrylate/(meth)acrylic acid/N-cyclohexylmaleimide copolymers, and 3-methyl-3-(meth)acryloyloxymethyloxetane/(meth)acrylic acid/styrene copolymers; resins [K3] such as benzyl (meth)acrylate/(meth)acrylic acid copolymers and styrene/(meth)acrylic acid copolymers; resins [K4] such as resins obtained by adding glycidyl (meth)acrylate to benzyl (meth)acrylate/(meth)acrylic acid copolymers, resins obtained by adding glycidyl (meth)acrylate to tricyclodecyl (meth)acrylate/styrene/(meth)acrylic acid copolymers, and resins obtained by adding glycidyl (meth)acrylate to tricyclodecyl (meth)acrylate/benzyl (meth)acrylate/(meth)acrylic acid copolymers; resins [K5] such as resins obtained by reacting tricyclodecyl (meth)acrylate/glycidyl (meth)acrylate copolymers with (meth)acrylic acid, and resins obtained by reacting tricyclodecyl (meth)acrylate/styrene/glycidyl (meth)acrylate copolymers with (meth)acrylic acid; and resins [K6] such as resins obtained by reacting tricyclodecyl (meth)acrylate/glycidyl (meth)acrylate copolymers with (meth)acrylic acid and further reacting the resulting resins with tetrahydrophthalic anhydride.

Among others, the resin (B) is preferably a resin [K1] or a resin [K2].

For example, the resin [K1] can be produced with reference to a method disclosed in the literature "Kobunshi Gosei no Jikkenho (Experimental Methods for Polymer Synthesis in English)" (Takayuki Otsu, Kagaku-Dojin Publishing Co., Inc., 1st edition, 1st issue, published on Mar. 1, 1972) and references cited in the literature.

The obtained copolymer may be used directly in the form of a solution after reaction. Alternatively, a concentrated or diluted solution thereof may be used, or a solid (powder) may be isolated by a method such as reprecipitation for use. Particularly, the solution after reaction can be used directly in the preparation of the colored resin composition of the present invention by using a solvent contained in the colored resin composition of the present invention as a solvent for this polymerization. This can simplify the process of producing the colored resin composition of the present invention.

The weight-average molecular weight of the resin (B) based on polystyrene is preferably 3,000 to 100,000, more preferably 5,000 to 50,000, further preferably 5,000 to 30,000. When the molecular weight falls within the range described above, there is a tendency for improved hardness of a color filter, a high residual film ratio, favorable solubility of an unexposed part in a developing solution, and improved resolution of a colored pattern.

The molecular weight distribution [weight-average molecular weight (Mw)/number-average molecular weight (Mn)] of the resin (B) is preferably 1.1 to 6, more preferably 1.2 to 4.

The acid number of the resin (B) is preferably 50 to 170 mg-KOH/g, more preferably 60 to 150, preferably 70 to 135 mg-KOH/g. In this context, the acid number is a value measured as the amount (mg) of potassium hydroxide necessary for neutralizing 1 g of the resin (B), and can be determined, for example, by titration using an aqueous potassium hydroxide solution.

The content of the resin (B) is preferably 10 to 90% by mass, more preferably 20 to 85% by mass, further preferably 30 to 80% by mass, based on the total amount of solid components. When the content of the resin (B) falls within the range described above, a colored pattern can be formed. Furthermore, a colored pattern resolution and a residual film ratio tend to be improved.

<Polymerizable Compound (C)>

The polymerizable compound (C) is a compound that is capable of being polymerized by an active radical and/or an acid generated from a polymerization initiator (D). Examples thereof include compounds having a polymerizable ethylenic unsaturated bond. A (meth)acrylic acid ester compound is preferred.

Among others, the polymerizable compound (C) is preferably a polymerizable compound having three or more ethylenic unsaturated bonds. Examples of such a polymerizable compound include:

compounds having one ethylenic unsaturated bond, such as nonylphenylcarbitol acrylate, 2-hydroxy-3-phenoxypropyl acrylate, 2-ethylhexylcarbitol acrylate, 2-hydroxyethyl acrylate, N-vinylpyrrolidone, and the compounds listed as examples of (Ba), (Bb) and (Bc) mentioned above;

compounds having two ethylenic unsaturated bonds, such as 1,6-hexanediol di(meth)acrylate, ethylene glycol di(meth)acrylate, neopentyl glycol di(meth)acrylate, triethylene glycol di(meth)acrylate, bis(acryloyloxyethyl) ether of bisphenol A and 3-methylpentanediol di(meth)acrylate;

compounds having three ethylenic unsaturated bonds, such as trimethylolpropane tri(meth)acrylate, pentaerythritol tri(meth)acrylate, and tris(2-(meth)acryloyloxyethyl) isocyanurate;

compounds having four ethylenic unsaturated bonds, such as pentaerythritol tetra(meth)acrylate, ethylene glycol-modified pentaerythritol tetra(meth)acrylate, propylene glycol-modified pentaerythritol tetra(meth)acrylate, and caprolactone-modified pentaerythritol tetra(meth)acrylate;

compounds having five ethylenic unsaturated bonds, such as dipentaerythritol penta(meth)acrylate;

compounds having six ethylenic unsaturated bonds, such as dipentaerythritol hexa(meth)acrylate, ethylene glycol-modified dipentaerythritol hexa(meth)acrylate, propylene glycol-modified dipentaerythritol hexa(meth)acrylate, and caprolactone-modified dipentaerythritol hexa(meth)acrylate; and compounds having seven or more ethylenic unsaturated bonds, such as tripentaerythritol hepta(meth)acrylate, tripentaerythritol octa(meth)acrylate, tetrapentaerythritol nona (meth)acrylate, and tetrapentaerythritol deca(meth)acrylate.

Among others, the polymerizable compound (C) is preferably a polymerizable compound having three or more ethylenic unsaturated bonds, more preferably a polymerizable compound having five or six ethylenic unsaturated bonds.

Among them, dipentaerythritol penta(meth)acrylate and dipentaerythritol hexa(meth)acrylate are particularly preferred.

The weight-average molecular weight of the polymerizable compound (C) is preferably 150 or higher and 2,900 or lower, more preferably 250 or higher and 1,500 or lower.

The content of the polymerizable compound (C) is preferably 7 to 65% by mass, more preferably 13 to 60% by mass, further preferably 17 to 55% by mass, based on the total amount of solid components. When the content of the polymerizable compound (C) falls within the range described above, a residual film ratio at the time of colored pattern formation and the chemical resistance of a color filter tend to be improved.

The content ratio between the resin (B) and the polymerizable compound (C) [resin (B):polymerizable compound (C)] is preferably 20:80 to 80:20, more preferably 35:65 to 80:20, based on mass.

<Polymerization Initiator (D)>

The polymerization initiator (D) is not particularly limited as long as the compound is capable of initiating polymerization by generating an active radical, an acid, or the like by the action of light or heat. A polymerization initiator known in the art can be used. Examples of the polymerization initiator that generates an active radical include O-acyl oxime compounds, alkylphenone compounds, triazine compounds, acylphosphine oxide compounds and biimidazole compounds.

The O-acyl oxime compound is a compound having a partial structure represented by the formula (Dd1). Hereinafter, * represents a bond.

[Formula 28]

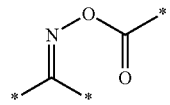
(Dd1)

Examples of the O-acyl oxime compound include N-benzoyloxy-1-(4-phenylsulfanylphenyl)butan-1-on-2-imine, N-benzoyloxy-1-(4-phenylsulfanylphenyl)octan-1-on-2-imine, N-benzoyloxy-1-(4-phenylsulfanylphenyl)-3-cyclopentylpropan-1-on-2-imine, N-acetoxy-1-[9-ethyl-6-(2-methylbenzoyl)-9H-carbazol-3-yl]ethan-1-imine, N-acetoxy-1-[9-ethyl-6-{2-methyl-4-(3,3-dimethyl-2,4-dioxacyclopentanylmethyloxy)benzoyl}-9H-carbazol-3-yl] ethan-1-imine, N-acetoxy-1-[9-ethyl-6-(2-methylbenzoyl)-9H-carbazol-3-yl]-3-cyclopentylpropan-1-imine, and N-benzoyloxy-1-[9-ethyl-6-(2-methylbenzoyl)-9H-carbazol-3-yl]-3-cyclopentylpropan-1-on-2-imine. A commercially available product such as Irgacure(R) OXE01 or OXE02 (both manufactured by BASF SE), or N-1919 (manufactured by Adeka Corp.) may be used. Among others, the O-acyl oxime compound is preferably at least one member selected from the group consisting of N-benzoyloxy-1-(4-phenylsulfanylphenyl)butan-1-on-2-imine, N-benzoyloxy-1-(4-phenylsulfanylphenyl)octan-1-on-2-imine and N-benzoyloxy-1-(4-phenylsulfanylphenyl)-3-cyclopentylpropan-1-on-2-imine, more preferably N-benzoyloxy-1-(4-phenylsulfanylphenyl)octan-1-on-2-imine. Use of such an O-acyl oxime compound tends to produce a color filter having high brightness.

The alkylphenone compound is a compound having a partial structure represented by the formula (Dd2) or a partial structure represented by the formula (Dd3). In these partial structures, the benzene ring may have a substituent.

[Formula 29]

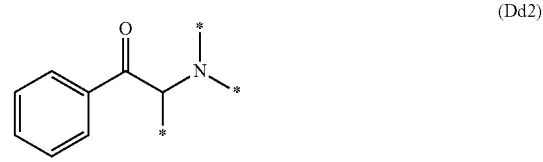
(Dd2)

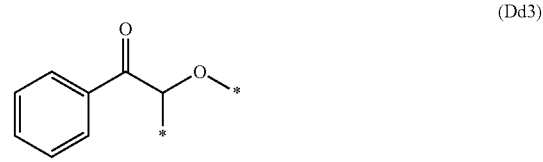
(Dd3)

Examples of the compound having a partial structure represented by the formula (Dd2) include 2-methyl-2-morpholino-1-(4-methylsulfanylphenyl)propan-1-one, 2-dimethylamino-1-(4-morpholinophenyl)-2-benzylbutan-1-one, and 2-(dimethylamino)-2-[(4-methylphenyl)methyl]-1-[4-(4-morpholinyl)phenyl]butan-1-one. A commercially available product such as Irgacure 369, 907, or 379 (all manufactured by BASF SE) may be used.

Examples of the compound having a partial structure represented by the formula (Dd3) include 2-hydroxy-2-methyl-1-phenylpropan-1-one, 2-hydroxy-2-methyl-1-[4-(2-hydroxyethoxy)phenyl]propan-1-one, 1-hydroxy cyclohexyl phenyl ketone, 2-hydroxy-2-methyl-1-(4-isopropenylphenyl)propan-1-one oligomers, α,α-diethoxyacetophenone, and benzyl dimethyl ketal.

The alkylphenone compound is preferably a compound having a partial structure represented by the formula (Dd2) from the viewpoint of sensitivity.

Examples of the triazine compound include 2,4-bis(trichloromethyl)-6-(4-methoxyphenyl)-1,3,5-triazine, 2,4-bis(trichloromethyl)-6-(4-methoxynaphthyl)-1,3,5-triazine, 2,4-bis(trichloromethyl)-6-piperonyl-1,3,5-triazine, 2,4-bis(trichloromethyl)-6-(4-methoxystyryl)-1,3,5-triazine, 2,4-bis(trichloromethyl)-6-[2-(5-methylfuran-2-yl)ethenyl]-1,3,5-triazine, 2,4-bis(trichloromethyl)-6-[2-(furan-2-yl)ethenyl]-1,3,5-triazine, 2,4-bis(trichloromethyl)-6-[2-(4- diethylamino-2-methylphenyl)ethenyl]-1,3,5-triazine, and 2,4-bis(trichloromethyl)-6-[2-(3,4-dimethoxyphenyl)ethenyl]-1,3,5-triazine.

Examples of the acylphosphine oxide compound include 2,4,6-trimethylbenzoyldiphenylphosphine oxide. A commercially available product such as Irgacure(R) 819 (manufactured by BASF SE) may be used.

Examples of the biimidazole compound include compounds represented by the formula (Dd4).

[Formula 30]

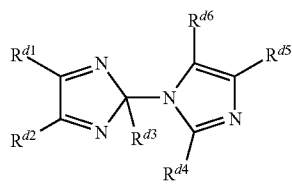

(Dd4)

wherein $R^{d1}$ to $R^{d6}$ each represent an aryl group having 6 to 10 carbon atoms and optionally having a substituent.

Examples of the aryl group having 6 to 10 carbon atoms represented by $R^{d1}$ to $R^{d6}$ include a phenyl group, a tolyl group, a xylyl group, an ethylphenyl group and a naphthyl group. A phenyl group is preferred.

Examples of the substituent by which the aryl group represented by $R^{d1}$ to $R^{d6}$ is optionally substituted include halogen atoms and alkoxy groups having 1 to 4 carbon atoms. Examples of the halogen atom include a fluorine atom, a chlorine atom, a bromine atom and an iodine atom. A chlorine atom is preferred. Examples of the alkoxy group having 1 to 4 carbon atoms include a methoxy group, an ethoxy group, a propoxy group and a butoxy group. A methoxy group is preferred.

Specific examples of the biimidazole compound include 2,2'-bis(2-chlorophenyl)-4,4',5,5'-tetraphenylbiimidazole, 2,2'-bis(2,3-dichlorophenyl)-4,4',5,5'-tetraphenylbiimidazole (see, for example, Japanese Patent Laid-Open Nos. 6-75372 and 6-75373), 2,2'-bis(2-chlorophenyl)-4,4',5,5'-tetraphenylbiimidazole, 2,2'-bis(2-chlorophenyl)-4,4',5,5'-tetra(alkoxyphenyl)biimidazole, 2,2'-bis(2-chlorophenyl)-4,4',5,5'-tetra(dialkoxyphenyl)biimidazole, 2,2'-bis(2-chlorophenyl)-4,4',5,5'-tetra(trialkoxyphenyl)biimidazole (see, for example, Japanese Patent Publication No. 48-38403 and Japanese Patent Laid-Open No. 62-174204), and biimidazole compounds with a phenyl group at 4,4',5,5'-position substituted by a carboalkoxy group (see, for example, Japanese Patent Laid-Open No. 7-10913). Among others, compounds represented by the following formulas and mixtures thereof are preferred.

[Formula 31]

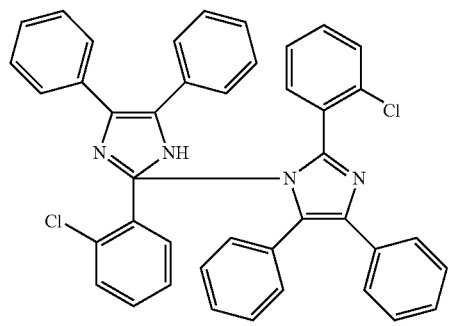

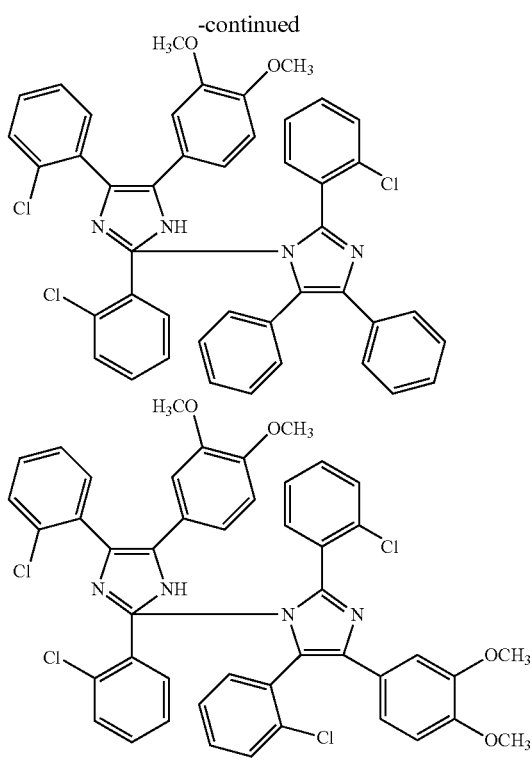

Further examples of the polymerization initiator (D) include: benzoin compounds such as benzoin, benzoin methyl ether, benzoin ethyl ether, benzoin isopropyl ether, and benzoin isobutyl ether; benzophenone compounds such as benzophenone, methyl o-benzoylbenzoate, 4-phenylbenzophenone, 4-benzoyl-4'-methyldiphenyl sulfide, 3,3',4,4'-tetra(tert-butylperoxycarbonyl)benzophenone, and 2,4,6-trimethylbenzophenone; quinone compounds such as 9,10-phenanthrenequinone, 2-ethylanthraquinone, and camphor quinone; and 10-butyl-2-chloroacridone, benzyl, methyl phenylglyoxylate, and titanocene compounds. These compounds are preferably used in combination with a polymerization initiation aid (D1) (particularly, amines) mentioned later.

Examples of the polymerization initiator that generates an acid include onium salts such as 4-hydroxyphenyldimethylsulfonium p-toluenesulfonate, 4-hydroxyphenyldimethylsulfonium hexafluoroantimonate, 4-acetoxyphenyldimethylsulfonium p-toluenesulfonate, 4-acetoxyphenylmethylbenzylsulfonium hexafluoroantimonate, triphenylsulfonium p-toluenesulfonate, triphenylsulfonium hexafluoroantimonate, diphenyliodonium p-toluenesulfonate, and diphenyliodonium hexafluoroantimonate, nitrobenzyl tosylates, and benzoin tosylates.

The polymerization initiator (D) is preferably a polymerization initiator that generates an active radical, more preferably a polymerization initiator comprising at least one member selected from the group consisting of an alkylphenone compound, a triazine compound, an acylphosphine oxide compound, an O-acyl oxime compound and a biimidazole compound, further preferably a polymerization initiator comprising an O-acyl oxime compound.

The content of the polymerization initiator (D) is preferably 0.1 to 30 parts by mass, more preferably 1 to 20 parts by mass, per 100 parts by mass in total of the resin (B) and the polymerizable compound (C). When the content of the polymerization initiator (D) falls within the range described above, an exposure time tends to be shortened because of higher sensitivity. Therefore, the productivity of a color filter is improved.

<Polymerization Initiation Aid (D1)>

The polymerization initiation aid (D1) is a compound that is used for promoting the polymerization of the polymerizable compound whose polymerization has been initiated by the polymerization initiator, or a sensitizer. The polymerization initiation aid (D1) comprised therein is usually used in combination with the polymerization initiator (D).

Examples of the polymerization initiation aid (D1) include amine compounds, alkoxyanthracene compounds, thioxanthone compounds and carboxylic acid compounds.

Examples of the amine compound include: alkanolamines such as triethanolamine, methyldiethanolamine, and triisopropanolamine; aminobenzoic acid esters such as methyl 4-dimethylaminobenzoate, ethyl 4-dimethylaminobenzoate, isoamyl 4-dimethylaminobenzoate, 2-dimethylaminoethyl benzoate, and 2-ethylhexyl 4-dimethylaminobenzoate; and alkylaminobenzophenones such as N,N-dimethyl-p-toluidine, 4,4'-bis(dimethylamino)benzophenone (commonly called Michler's ketone), 4,4'-bis(diethylamino)benzophenone, and 4,4'-bis(ethylmethylamino)benzophenone. Among them, alkylaminobenzophenone is preferred, and 4,4'-bis(diethylamino)benzophenone is preferred. A commercially available product such as EAB-F (manufactured by Hodogaya Chemical Co., Ltd.) may be used.

Examples of the alkoxyanthracene compound include 9,10-dimethoxyanthracene, 2-ethyl-9,10-dimethoxyanthracene, 9,10-diethoxyanthracene, 2-ethyl-9,10-diethoxyanthracene, 9,10-dibutoxyanthracene, and 2-ethyl-9,10-dibutoxyanthracene.

Examples of the thioxanthone compound include 2-isopropylthioxanthone, 4-isopropylthioxanthone, 2,4-diethylthioxanthone, 2,4-dichlorothioxanthone, and 1-chloro-4-propoxythioxanthone.

Examples of the carboxylic acid compound include phenylsulfanylacetic acid, methylphenylsulfanylacetic acid, ethylphenylsulfanylacetic acid, methylethylphenylsulfanylacetic acid, dimethylphenylsulfanylacetic acid, methoxyphenylsulfanylacetic acid, dimethoxyphenylsulfanylacetic acid, chlorophenylsulfanylacetic acid, dichlorophenylsulfanylacetic acid, N-phenylglycine, phenoxyacetic acid, naphthylthioacetic acid, N-naphthylglycine, and naphthoxyacetic acid.

In the case of using such a polymerization initiation aid (D1), the content thereof is preferably 0.1 to 30 parts by mass, more preferably 1 to 20 parts by mass, per to 100 parts by mass in total of the resin (B) and the polymerizable compound (C). When the amount of the polymerization initiation aid (D1) falls within this range, a colored pattern can be formed with higher sensitivity. Thus, the productivity of a color filter tends to be improved.

<Solvent (E)>

The solvent (E) is not particularly limited, and solvents usually used in the art can be used singly or in combinations of two or more thereof. Examples thereof include ester solvents (solvents containing —COO— in the molecule and containing no —O—), ether solvents (solvents containing —O— in the molecule and containing no —COO—), ether ester solvents (solvents containing —COO— and —O— in the molecule), ketone solvents (solvents containing —CO— in the molecule and containing no —COO—), alcohol solvents (solvents containing OH in the molecule and containing none of —O—, —CO— and —COO—), aromatic hydrocarbon solvents, amide solvents, and dimethyl sulfoxide.

Examples of the ester solvent include methyl lactate, ethyl lactate, butyl lactate, methyl 2-hydroxyisobutanoate, ethyl acetate, n-butyl acetate, isobutyl acetate, pentyl formate, isopentyl acetate, butyl propionate, isopropyl butyrate, ethyl butyrate, butyl butyrate, methyl pyruvate, ethyl pyruvate, propyl pyruvate, methyl acetoacetate, ethyl acetoacetate, cyclohexanol acetate and γ-butyrolactone.

Examples of the ether solvent include ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, diethylene glycol monobutyl ether, propylene glycol monomethyl ether, propylene glycol monoethyl ether, propylene glycol monopropyl ether, propylene glycol monobutyl ether, 3-methoxy-1-butanol, 3-methoxy-3-methylbutanol, tetrahydrofuran, tetrahydropyran, 1,4-dioxane, diethylene glycol dimethyl ether, diethylene glycol diethyl ether, diethylene glycol methyl ethyl ether, diethylene glycol dipropyl ether, diethylene glycol dibutyl ether, anisole, phenetole and methylanisole.

Examples of the ether ester solvent include methyl methoxyacetate, ethyl methoxyacetate, butyl methoxyacetate, methyl ethoxyacetate, ethyl ethoxyacetate, methyl 3-methoxypropionate, ethyl 3-methoxypropionate, methyl 3-ethoxypropionate, ethyl 3-ethoxypropionate, methyl 2-methoxypropionate, ethyl 2-methoxypropionate, propyl 2-methoxypropionate, methyl 2-ethoxypropionate, ethyl 2-ethoxypropionate, methyl 2-methoxy-2-methylpropionate, ethyl 2-ethoxy-2-methylpropionate, 3-methoxybutyl acetate, 3-methyl-3-methoxybutyl acetate, propylene glycol monomethyl ether acetate, propylene glycol monoethyl ether acetate, propylene glycol monopropyl ether acetate, ethylene glycol monomethyl ether acetate, ethylene glycol monoethyl ether acetate, diethylene glycol monoethyl ether acetate, diethylene glycol monobutyl ether acetate and dipropylene glycol methyl ether acetate.

Examples of the ketone solvent include 4-hydroxy-4-methyl-2-pentanone, acetone, 2-butanone, 2-heptanone, 3-heptanone, 4-heptanone, 4-methyl-2-pentanone, cyclopentanone, cyclohexanone and isophorone.

Examples of the alcohol solvent include methanol, ethanol, propanol, butanol, hexanol, cyclohexanol, ethylene glycol, propylene glycol and glycerin.

Examples of the aromatic hydrocarbon solvent include benzene, toluene, xylene and mesitylene.

Examples of the amide solvent include N,N-dimethylformamide, N,N-dimethylacetamide and N-methylpyrrolidone.

Among the solvents described above, an organic solvent having a boiling point of 120° C. or higher and 210° C. or lower at 1 atm is preferred from the viewpoint of coatability and dryability. The solvent is preferably propylene glycol monomethyl ether acetate, ethyl lactate, propylene glycol monomethyl ether, ethyl 3-ethoxypropionate, ethylene glycol monomethyl ether, ethylene glycol monobutyl ether, diethylene glycol monomethyl ether, diethylene glycol monoethyl ether, 3-methoxybutyl acetate, 3-methoxy-1-butanol, 4-hydroxy-4-methyl-2-pentanone, N-methylpyrrolidone or N,N-dimethylformamide, more preferably propylene glycol monomethyl ether acetate, propylene glycol monomethyl ether, ethyl 3-ethoxypropionate, N-methylpyrrolidone, or N,N-dimethylformamide.

The content of the solvent (E) is preferably 70 to 95% by mass, more preferably 75 to 92% by mass, based on the total amount of the colored resin composition of the present invention. In other words, the total amount of solid components in the colored resin composition is preferably 5 to 30% by mass, more preferably 8 to 25% by mass. When the content of the solvent (E) falls within the range described above, display characteristics tend to be favorable because of favorable flatness at the time of coating and no lack of a color density in a formed color filter.

<Leveling Agent (F)>

Examples of the leveling agent (F) include silicone surfactants, fluorine surfactants and silicone surfactants having a fluorine atom. These leveling agents may have a polymerizable group in a side chain.

Examples of the silicone surfactant include surfactants having a siloxane bond in the molecule. Specific examples thereof include Toray Silicone DC3PA, Toray Silicone SH7PA, Toray Silicone DC11PA, Toray Silicone SH21PA, Toray Silicone SH28PA, Toray Silicone SH29PA, Toray Silicone SH30PA, and Toray Silicone SH8400 (trade name; manufactured by Dow Corning Toray Co., Ltd.), KP321, KP322, KP323, KP324, KP326, KP340, and KP341 (manufactured by Shin-Etsu Chemical Co., Ltd.), and TSF400, TSF401, TSF410, TSF4300, TSF4440, TSF4445, TSF-4446, TSF4452 and TSF4460 (manufactured by Momentive Performance Materials Japan LLC).

Examples of the fluorine surfactant include surfactants having a fluorocarbon chain in the molecule. Specific examples thereof include Fluorad (R) FC430 and Fluorad FC431(manufactured by Sumitomo 3M Ltd.), MEGAFACE (R) F142D, MEGAFACE F171, MEGAFACE F172, MEGAFACE F173, MEGAFACE F177, MEGAFACE F183, MEGAFACE F554, MEGAFACE R30, and MEGAFACE RS-718-K (manufactured by DIC Corp.), EFTOP (R) EF301, EFTOP EF303, EFTOP EF351, and EFTOP EF352 (manufactured by Mitsubishi Materials Electronic Chemicals Co., Ltd.), Surflon (R) S381, Surflon S382, Surflon SC101, and Surflon SC105 (manufactured by AGC Inc.) and E5844 (manufactured by Daikin Fine Chemical Laboratory Co., Ltd.).

Examples of the silicone surfactant having a fluorine atom include surfactants having a siloxane bond and a fluorocarbon chain in the molecule. Specific examples thereof include MEGAFACE(R) R08, MEGAFACE BL20, MEGAFACE F475, MEGAFACE F477 and MEGAFACE F443 (manufactured by DIC Corp.).

The content of the leveling agent (F) is preferably 0.0001% by mass or more and 0.2% by mass or less, more preferably 0.0002% by mass or more and 0.1% by mass or less, further preferably 0.0003% by mass or more and 0.05% by mass or less, based on the total amount of the colored resin composition. This content excludes the content of the pigment dispersant. When the content of the leveling agent (F) falls within the range described above, the resulting color filter can have favorable flatness.

<Other Components>

The colored resin composition of the present invention may optionally comprise additives known in the art, such as a filler, other polymer compounds, an adhesion promoter, an antioxidant, a light stabilizer, and a chain transfer agent.

<Method for Producing Colored Resin Composition>

The colored resin composition of the present invention can be prepared, for example, by mixing the colorant (A), the resin (B), the solvent (E), and the leveling agent (F), and if patterning is performed by a photolithography method, further the polymerizable compound (C), the polymerization initiator (D), the polymerization initiation aid (D1) and other components.

The pigment (A-2) is preferably mixed in advance with a portion or the whole of the solvent (E) and dispersed using a bead mill or the like until the average particle size of the pigment becomes approximately 0.2 or smaller. In this operation, a portion or the whole of the pigment dispersant and the resin (B) may be blended therewith, if necessary. The pigment dispersion thus obtained can be mixed with the remaining components such that predetermined concentrations are attained to prepare the colored resin composition of interest.

Each dye may be dissolved in advance in a portion or the whole of the solvent (E) to prepare a solution. The solution is preferably filtered through a filter having a pore size on the order of 0.01 to 1 μm.

The colored resin composition thus mixed is preferably filtered through a filter having a pore size on the order of 0.1 to 10 μm.

<Method for Producing Color Filter>

Examples of the method for producing a color filter from the colored resin composition of the present invention include a method comprising coating a substrate with the colored resin composition, and removing volatile components such as the solvent by drying by heating (prebaking) and/or drying under reduced pressure while drying the substrate to form a smooth colored composition layer, followed by postbaking. The colored coating film thus formed can be the color filter of the present invention.

A glass plate such as quartz glass, borosilicate glass, aluminasilicate glass, or soda-lime glass surface-coated with silica, a resin plate such as polycarbonate, methyl polymethacrylate, or polyethylene terephthalate, silicon, or such a substrate with an aluminum, silver, or silver/copper/palladium alloy thin film, etc. formed thereon is used as the substrate. Another color filter layer, a resin layer, a transistor, a circuit, and the like may be formed on these substrates.

Examples of the coating method include a spin coating method, a slit coating method, and a slit and spin coating method.

In the case of performing drying by heating, the temperature is preferably 30 to 120° C., more preferably 50 to 110° C. The heating time is preferably 10 seconds to 60 minutes, more preferably 30 seconds to 30 minutes.

In the case of performing drying under reduced pressure, preferably, the pressure is 50 to 150 Pa, and the temperature is in the range of 20 to 25° C.

The film thickness of the colored resin composition is not particularly limited and can be appropriately selected according to the film thickness of the color filter of interest.

The obtained film of the colored resin composition is preferably postbaked. The postbaking temperature is preferably 150 to 250° C., more preferably 160 to 235° C. The postbaking time is preferably 1 to 120 minutes, more preferably 10 to 60 minutes.

The film thickness of the resulting color filter is not particularly limited and can be appropriately adjusted according to a purpose, application, etc. The film thickness is, for example, 0.1 to 30 μm, preferably 0.1 to 20 μm, more preferably 0.5 to 6 μm.

The cured coating film thus obtained may be patterned by, for example, an etching method.

A colored pattern may be produced by a photolithography method, an inkjet method, a printing method, or the like using the colored resin composition of the present invention. Among them, a photolithography method is preferred when the colored resin composition comprises the polymerizable compound (C) and the polymerization initiator (D). The photolithography method is a method comprising coating a substrate with the colored resin composition, drying the substrate to form a colored composition layer, and exposing the colored composition layer via a photomask for development. The coating and the drying can be performed under the conditions mentioned above.

The colored composition layer is exposed via a photomask for forming the colored pattern of interest. The pattern on the photomask is not particularly limited, and a pattern appropriate for the application of interest is used.

The light source for use in exposure is preferably a light source that generates light with a wavelength of 250 to 450 nm. For example, light shorter than 350 nm may be cut using a filter that cuts this wavelength region, or light around 436 nm, around 408 nm, and around 365 nm may be selectively extracted using bandpass filters that extract these wavelength regions. Specific examples thereof include mercury-vapor lamps, light-emitting diodes, metal halide lamps, and halogen lamps.

Exposure apparatuses such as a mask aligner and a stepper are preferably used because the whole exposure surface can be uniformly irradiated with parallel light beam, or the photomask and the substrate with the colored composition layer formed thereon can be accurately aligned.

The colored composition layer thus exposed is developed by contact with a developing solution to form a colored pattern on the substrate. By the development, an unexposed part of the colored composition layer is dissolved in the developing solution and removed. Examples of the developing solution include aqueous solutions of alkaline compounds such as potassium hydroxide, sodium bicarbonate, sodium carbonate, and tetramethylammonium hydroxide. The concentration of such an alkaline compound in the aqueous solution is preferably 0.01 to 10% by mass, more preferably 0.03 to 5% by mass. The developing solution may further contain a surfactant.

The development method can be any of paddle, dipping and spraying methods, etc. The substrate may be tilted with an arbitrary angle at the time of development The colored pattern thus developed is preferably washed with water.

The obtained colored pattern is preferably postbaked. The postbaking temperature and time can be the same as those mentioned above.

According to the colored resin composition comprising the colorant comprising the compound of the present invention, a thinned color filter can be prepared as compared with the case of using a conventional colored resin composition. The color filter is useful as a color filter for use in solid-state imaging devices and display apparatuses (e.g., liquid-crystal display apparatuses, organic EL apparatuses, and electronic papers).

EXAMPLES

Hereinafter, the present invention will be described in more detail with reference to Examples. However, the present invention is not limited by these Examples. In the examples, the terms "%" and "parts" which represent a content or an amount used are based on mass unless otherwise specified.

In the synthesis examples given below, the structures of compounds were identified by mass spectrometry (LC; model 1100 manufactured by Agilent Technologies, Inc., MASS; model LC/MSD manufactured by Agilent Technologies, Inc.) and NMR (JNM-ECA400; manufactured by JEOL Ltd.).

Example 1

Compound Represented by Formula (I-1)

A 300 mL four-neck flask was charged with 7.00 parts of 2,4-difluoroaniline (manufactured by Tokyo Chemical Industry Co., Ltd.), 10.14 parts of 3-bromoanisole (manufactured by Tokyo Chemical Industry Co., Ltd.), 0.61 parts of palladium acetate (manufactured by Tokyo Chemical Industry Co., Ltd.), 3.86 parts of a 1 M solution of tertiary butylphosphine in hexane (manufactured by Tokyo Chemical Industry Co., Ltd.), and 101.41 parts of toluene (manufactured by Nacalai Tesque, Inc.) and stirred at 40° C. for 5 minutes. The four-neck flask was charged with 7.82 parts of sodium tertiary butoxide (manufactured by Tokyo Chemical Industry Co., Ltd.) and stirred at 110° C. for 10 hours. The mixture was cooled to room temperature, and the solvent was distilled off under reduced pressure. The residue was separated into organic and aqueous layers by the addition of 100 parts of ethyl acetate and 100 parts of water, and the ethyl acetate layer was isolated. The ethyl acetate layer was separated into organic and aqueous layers by the addition of 20 parts of ethyl acetate and 50 parts of water, and the ethyl acetate layer was isolated. Ethyl acetate was distilled off under reduced pressure. To the obtained residue, 20 parts of hexane were added, and a black solid insoluble in hexane was filtered off. Sodium sulfate was added to the hexane solution for dehydration and then filtered off, and hexane was distilled off under reduced pressure. The obtained residue was purified by silica gel chromatography (ethyl acetate/hexane=1/10), and the obtained oil substance was dried under reduced pressure at 60° C. for 24 hours to obtain 8.16 parts of a compound represented by the formula (a-1-1) (yield: 64.0%).

(Mass spectrometry) Ionization mode=ESI+: m/z=[M+H]$^+$ 236.1

[Formula 32]

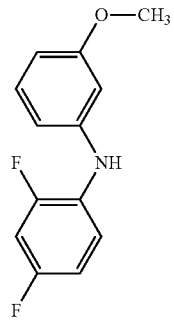

(a-1-1)

A 50 mL four-neck flask was charged with 3.60 parts of the compound represented by the formula (a-1-1), 4.29 parts of potassium hydroxide (manufactured by Wako Pure Chemical Industries, Ltd.), and 12.00 parts of dimethyl sulfoxide (manufactured by Kanto Chemical Co., Inc.) and stirred at 20° C. for 30 minutes. The four-neck flask was charged with 8.87 parts of 1-bromo-2-ethylhexane (manufactured by Tokyo Chemical Industry Co., Ltd.) and stirred at 20° C. for 9 hours. The flask was charged with 25 parts of water under ice cooling. The mixture was separated into organic and aqueous layers by the addition of 25 parts of ethyl acetate, and the ethyl acetate layer was isolated. This operation of separation into organic and aqueous layers was repeated a total of three times, and the ethyl acetate layers were combined. The ethyl acetate layer was separated into organic and aqueous layers by the addition of 25 parts of water, and the ethyl acetate layer was isolated. This operation of separation into organic and aqueous layers was repeated a total of four times. Sodium sulfate was added to the ethyl acetate layer for dehydration and then filtered off, and ethyl acetate was distilled off under reduced pressure. The obtained residue was purified by silica gel chromatography (toluene/hexane=1/5), and the obtained oil substance was dried under reduced pressure at 60° C. for 24 hours to obtain 4.73 parts of a compound represented by the formula (a-1-2) (yield: 89.0%).

(Mass spectrometry) Ionization mode=ESI+: m/z=[M+H]$^+$ 348.2

[Formula 33]

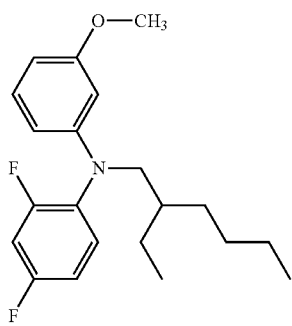

(a-1-2)

A 100 mL four-neck flask was charged with 2.00 parts of the compound represented by the formula (a-1-2) and 20.00 parts of dehydrated methylene chloride (manufactured by Wako Pure Chemical Industries, Ltd.) and stirred at 20° C. for 10 minutes. While the four-neck flask was cooled in ice, 11.88 parts of a 17 wt % solution of boron tribromide in methylene chloride (manufactured by Wako Pure Chemical Industries, Ltd.) was added dropwise thereto such that the internal temperature did not exceed 10° C. The flask was stirred at 20° C. for 5 hours. Another 200 mL four-neck flask was charged with 20 parts of methylene chloride and 25 parts of water, and the reaction solution was added dropwise thereto under ice cooling such that the internal temperature did not exceed 10° C. The mixture was stirred at 20° C. for 2 hours, and the methylene chloride layer was isolated. The methylene chloride layer was separated into organic and aqueous layers by the addition of 40 parts of 10 wt % saline, and the ethyl acetate layer was isolated. This operation of separation into organic and aqueous layers was repeated a total of four times. Sodium sulfate was added to the ethyl acetate layer for dehydration and then filtered off, and ethyl acetate was distilled off under reduced pressure. The obtained oil substance was dried under reduced pressure at 60° C. for 24 hours to obtain 1.84 parts of a compound represented by the formula (a-1-3) (yield: 95.9%).

(Mass spectrometry) Ionization mode=ESI+: m/z=[M+H]$^+$ 334.2

[Formula 34]

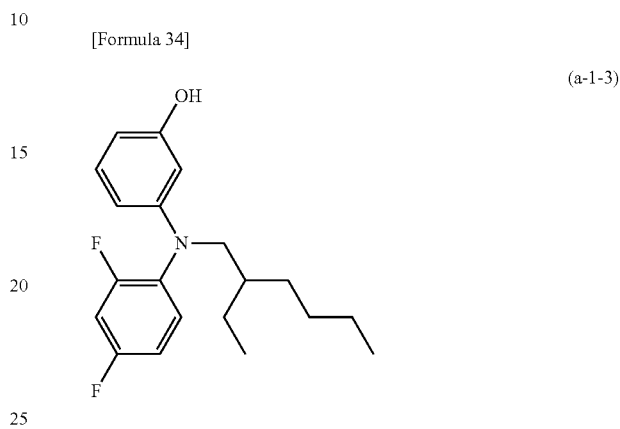

(a-1-3)

A 100 mL four-neck flask was charged with 1.84 g of the compound represented by the formula (a-1-3), 0.31 g of 3,4-dihydroxy-3-cyclobutene-1,2-dione (manufactured by Wako Pure Chemical Industries, Ltd.), 27.00 g of 1-butanol (manufactured by Wako Pure Chemical Industries, Ltd.), and 18.00 g of toluene (manufactured by Nacalai Tesque, Inc.) and stirred at 115° C. for 12 hours while produced water was removed using a Dean-Stark tube. After the completion of reaction, the solvent was distilled off under reduced pressure. To the obtained residue, 50 parts of water were added, and the mixture was stirred. Water was removed by decantation. To the obtained residue, 72 parts of a mixed solvent of ethyl acetate/hexane=1/7 were added, and the mixture was stirred. A solid was filtered off and dried under reduced pressure at 60° C. or 24 hours to obtain 0.92 g of a compound represented by the formula (I-1) (yield: 45.7%).

(Mass spectrometry) Ionization mode=ESI+: m/z=[M+H]$^+$ 745.4

Compound represented by the formula (I-1): $^1$H-NMR (400 MHz, δ value (ppm, referenced to TMS), CDCl$_3$) 0.82-0.88 (m,12H), 1.18-1.46 (m,16H), 1.68 (m,2H), 3.61 (d,4H), 6.07 (s,2H), 6.22 (d,2H), 6.98 (m,4H), 7.24 (m,2H), 7.84 (d,1H), 7.99 (d,1H), 11.43 (s,1H), 12.14 (s, 1H)

[Formula 35]

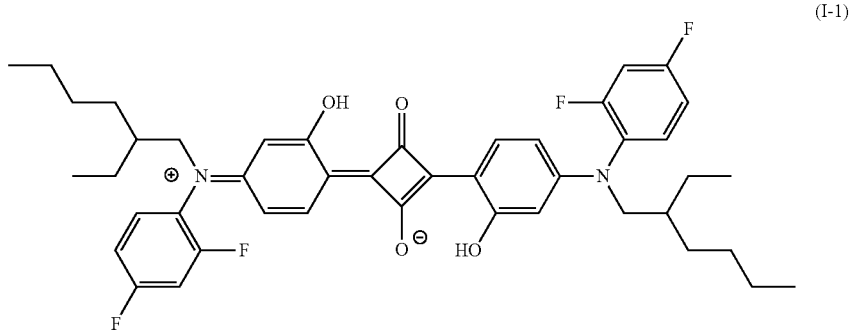

(I-1)

Example 2

Compound Represented by Formula (I-13)

9.86 g of a compound represented by the formula (a-13-1) was obtained (yield: 78.4%) by the same operation as in Example 1 except that 2,4-difluoroaniline was changed to 10.00 parts of 2,6-difluoroaniline (manufactured by Tokyo Chemical Industry Co., Ltd.).

(Mass spectrometry) Ionization mode=ESI+: m/z=[M+H]$^+$ 236.1

[Formula 36]

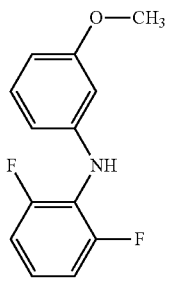

(a-13-1)

5.57 g of a compound represented by the formula (a-13-2) was obtained (yield: 85.6%) by the same operation as in Example 1 except that the compound represented by the formula (a-1-1) was changed to 4.81 parts of the compound represented by the formula (a-13-1).

(Mass spectrometry) Ionization mode=ESI+: m/z=[M+H]$^+$0 348.2

[Formula 37]

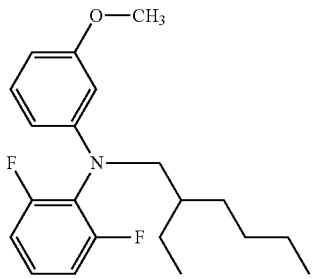

(a-13-2)

6.31 g of a compound represented by the formula (a-13-3) was obtained (yield: 99.6%) by the same operation as in Example 1 except that the compound represented by the formula (a-1-2) was changed to 6.60 parts of the compound represented by the formula (a-13-2).

(Mass spectrometry) Ionization mode=ESI+: m/z=[M+H]$^+$ 334.2

[Formula 38]

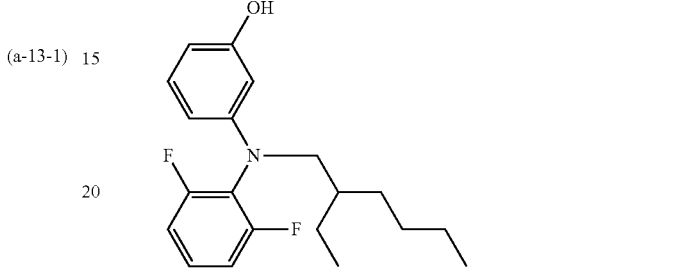

(a-13-3)

A 300 mL four-neck flask was charged with 6.00 g of the compound represented by the formula (a-13-3), 1.01 g of 3,4-dihydroxy-3-cyclobutene-1,2-dione (manufactured by Wako Pure Chemical Industries, Ltd.), 90.00 g of 1-butanol (manufactured by Wako Pure Chemical Industries, Ltd.), and 60.00 g of toluene (manufactured by Nacalai Tesque, Inc.) and stirred at 115° C. for 15 hours while produced water was removed using a Dean-Stark tube. After the completion of reaction, the solvent was distilled off under reduced pressure. The obtained residue was purified by silica gel chromatography (chloroform/hexane=9/4). The obtained residue was recrystallized from hexane, and the obtained solid was filtered off and dried under reduced pressure at 60° C. for 24 hours to obtain 1.67 g of a compound represented by the formula (I-13) (yield: 25.4%).

(Mass spectrometry) Ionization mode=ESI+: m/z=[M+H]$^+$ 745.4

Compound represented by the formula (I-13): $^1$H-NMR (400 MHz, δ value (ppm, referenced to TMS), CDCl$_3$) 0.81-0.87 (m,12H), 1.21-1.47 (m,16H), 1.66 (m,2H), 3.62 (d,4H), 6.10 (s,2H), 6.26 (d,2H), 7.06 (t,4H), 7.37 (m,2H), 7.88 (d,1H), 8.02 (d,1H), 11.45 (s,1H), 12.17 (s, 1H)

[Formula 39]

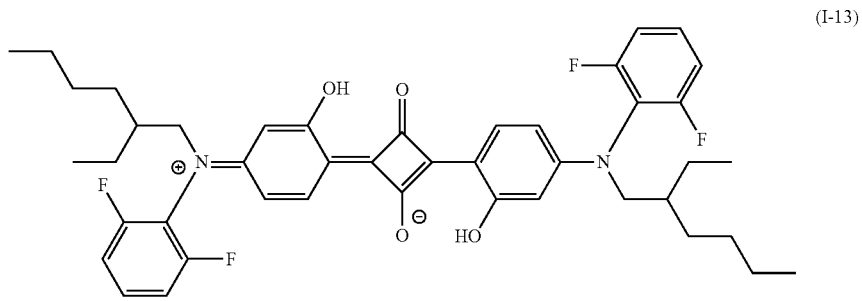

(I-13)

Example 3

Compound Represented by Formula (I-7)

29.84 g of a compound represented by the formula (a-7-1) was obtained (yield: 81.9%) by the same operation as in Example 1 except that 2,4-difluoroaniline was changed to 20.00 parts of 2,5-difluoroaniline (manufactured by Tokyo Chemical Industry Co., Ltd.).

(Mass spectrometry) Ionization mode=ESI+: m/z=[M+H]$^+$ 236.1

[Formula 40]

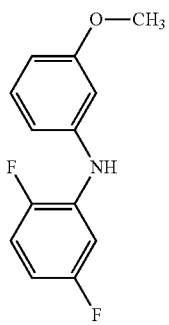

(a-7-1)

25.87 g of a compound represented by the formula (a-7-2) was obtained (yield: 98.2%) by the same operation as in Example 1 except that the compound represented by the formula (a-1-1) was changed to 20.00 parts of the compound represented by the formula (a-7-1).

(Mass spectrometry) Ionization mode=ESI+: m/z=[M+H]$^+$ 348.2

[Formula 41]

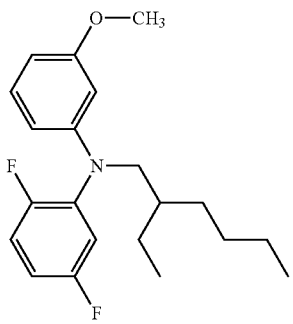

(a-7-2)

13.01 g of a compound represented by the formula (a-7-3) was obtained (yield: 90.4%) by the same operation as in Example 1 except that the compound represented by the formula (a-1-2) was changed to 15.00 parts of the compound represented by the formula (a-7-2).

(Mass spectrometry) Ionization mode=ESI+: m/z=[M+H]$^+$ 334.2

[Formula 42]

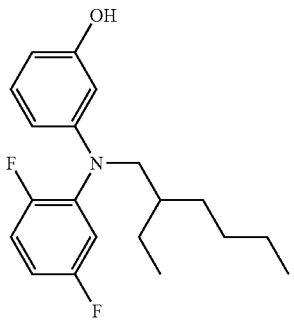

(a-7-3)

A 1000 mL four-neck flask was charged with 11.00 g of the compound represented by the formula (a-7-3), 1.84 g of 3,4-dihydroxy-3-cyclobutene-1,2-dione (manufactured by Wako Pure Chemical Industries, Ltd.), 180.00 g of 1-butanol (manufactured by Wako Pure Chemical Industries, Ltd.), and 120.00 g of toluene (manufactured by Nacalai Tesque, Inc.) and stirred at 115° C. for 10 hours while produced water was removed using a Dean-Stark tube. After the completion of reaction, the solvent was distilled off under reduced pressure. The obtained residue was purified by washing with water and hexane. The obtained solid was filtered off and dried under reduced pressure at 60° C. or 24 hours to obtain 4.06 g of a compound represented by the formula (I-7) (yield: 33.7%).

(Mass spectrometry) Ionization mode=ESI+: m/z=[M+H]$^+$ 745.4

Compound represented by the formula (I-7): $^1$H-NMR (400 MHz, δ value (ppm, referenced to TMS), CDCl$_3$) 0.80-0.85 (m,12H), 1.16-1.42 (m,16H), 1.68-1.71 (m,2H), 3.63 (d,4H), 6.09 (s,2H), 6.24 (d,2H), 6.99 (m,2H), 7.05 (m,2H), 7.17 (m,2H), 7.84 (d,1H), 7.99 (d,1H), 11.43 (s,1H), 12.15 (s,1H)

[Formula 43]

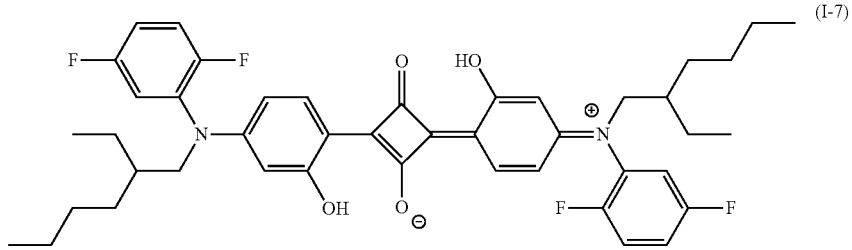

(I-7)

Example 4

Compound Represented by Formula (I-19)

14.33 g of a compound represented by the formula (a-19-1) was obtained (yield: 23.8%) by the same operation as in Example 1 except that 2,4-difluoroaniline was changed to 25.00 parts of 2-aminobenzotrifluoride (manufactured by Tokyo Chemical Industry Co., Ltd.).

(Mass spectrometry) Ionization mode=ESI+: m/z=[M+H]$^+$ 268.1

[Formula 44]

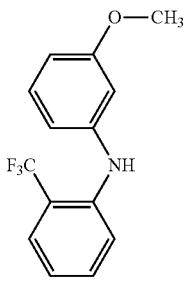

(a-19-1)

3.71 g of a compound represented by the formula (a-19-2) was obtained (yield: 62.8%) by the same operation as in Example 1 except that the compound represented by the formula (a-1-1) was changed to 7.00 parts of the compound represented by the formula (a-19-1).

(Mass spectrometry) Ionization mode=ESI+: m/z=[M+H]$^+$ 380.2

[Formula 45]

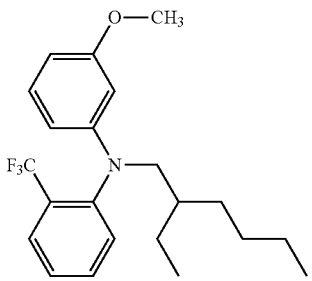

(a-19-2)

2.32 g of a compound represented by the formula (a-19-3) was obtained (yield: 64.9%) by the same operation as in Example 1 except that the compound represented by the formula (a-1-2) was changed to 3.71 parts of the compound represented by the formula (a-19-2).

(Mass spectrometry) Ionization mode=ESI+: m/z=[M+H]$^+$ 366.2

[Formula 46]

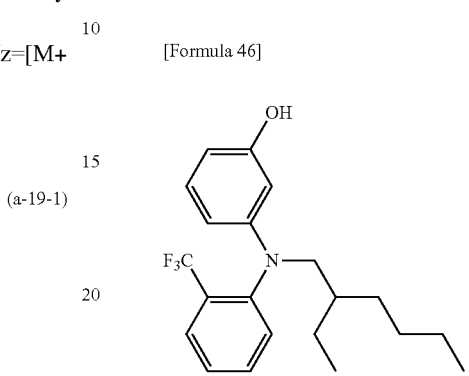

(a-19-3)

A 200 mL four-neck flask was charged with 2.30 g of the compound represented by the formula (a-19-3), 0.35 g of 3,4-dihydroxy-3-cyclobutene-1,2-dione (manufactured by Wako Pure Chemical Industries, Ltd.), 33.00 g of 1-butanol (manufactured by Wako Pure Chemical Industries, Ltd.), and 22.00 g of toluene (manufactured by Nacalai Tesque, Inc.) and stirred at 115° C. for 10 hours while produced water was removed using a Dean-Stark tube. After the completion of reaction, the solvent was distilled off under reduced pressure. To the obtained residue, 30 parts of water were added, and the mixture was stirred. Water was removed by decantation. The obtained residue was purified by silica gel chromatography (chloroform/hexane=1/1). The residue was dried under reduced pressure at 60° C. for 24 hours to obtain 0.80 g of a compound represented by the formula (I-19) (yield: 32.1%).

(Mass spectrometry) Ionization mode=ESI+: m/z=[M+H]$^+$ 809.4

Compound represented by the formula (I-19): $^1$H-NMR (400 MHz, δ value (ppm, referenced to TMS), CDCl$_3$) 0.72-0.92 (m,12H), 1.17-1.44 (m,16H), 1.77 (m,2H), 3.27 (m,2H), 3.90 (m,2H), 5.92 (s,2H), 6.09 (s,2H), 7.31 (t,2H), 7.54 (t,2H), 7.67 (t,2H), 7.80 (t,4H), 11.38 (s,1H), 12.10 (s,1H)

[Formula 47]

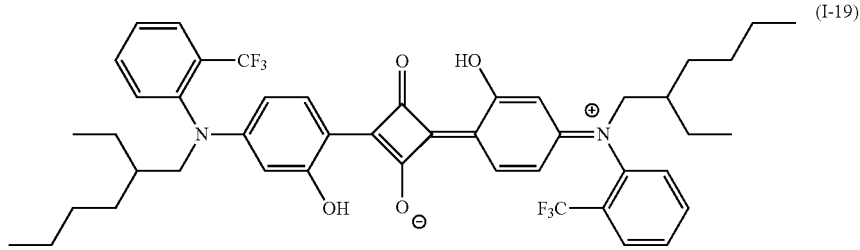

(I-19)

Comparative Example 1

Compound Represented by Formula (I'-1)

A compound represented by the following formula (I'-1) was produced by the method disclosed in Japanese Patent Laid-Open No. 2015-86379.

[Formula 48]

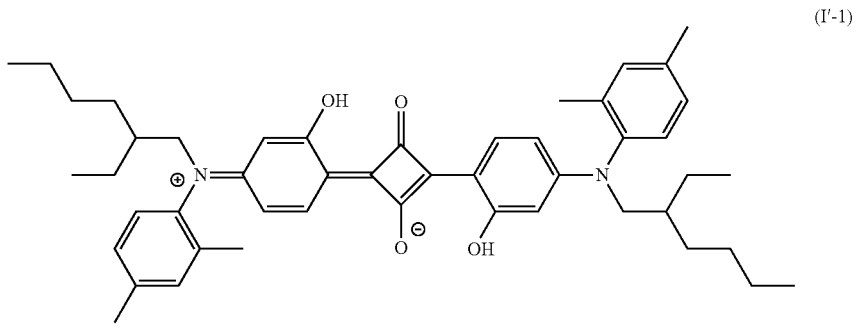

(I'-1)

0.35 g of the compound represented by the formula (I-1) was dissolved in chloroform to adjust the volume to 250 cm$^3$, 2 cm$^3$ of which was diluted with chloroform to adjust the volume 100 cm$^3$ (concentration: 0.028 g/L). Absorption spectra were measured using a spectrophotometer (quartz cell, optical path length: 1 cm). This compound had λmax=639 nm.

The absorption spectra of the compound represented by the formula (I-13) were measured in the same way as above. This compound had λmax=636 nm.

The absorption spectra of the compound represented by the formula (I-7) were measured in the same way as above. This compound had λmax=640 nm.

The absorption spectra of the compound represented by the formula (I-19) were measured in the same way as above. This compound had λmax=638 nm.

The absorption spectra of the compound represented by the formula (I'-1) were measured in the same way as above. This compound had λmax=649 nm.

Absorbance at 640 nm around λmax of the absorption spectra measured for the compounds represented by the formulas (I-1), (I-13), (I-7), (I-19) and (I'-1) is shown in Table 2.

TABLE 2

| | Compound | Absorbance at 640 nm |
|---|---|---|
| Example 1 | I-1 | 11.6 |
| Example 2 | I-13 | 11.9 |
| Example 3 | I-7 | 13.2 |
| Example 4 | I-19 | 12.9 |
| Comparative Example 1 | I'-1 | 9.8 |

[Synthesis of Resin B-1]

The atmosphere in a flask equipped with a reflux condenser, a dropping funnel and a stirrer was purged with an appropriate amount of nitrogen, and 290 parts of propylene glycol monomethyl ether acetate were placed therein and heated to 85° C. with stirring. Subsequently, a mixed solution of 94 parts of a mixture of 3,4-epoxytricyclo[5.2.1.0$^{2,6}$]decan-8-yl acrylate and 3,4-epoxytricyclo[5.2.1.0$^{2,6}$]decan-9-yl acrylate (content ratio: 1:1), 61 parts of 4-vinylbenzoic acid, 157 parts of phenyl methacrylate, and 250 parts of propylene glycol monomethyl ether acetate was added dropwise thereto over 4 hours. Meanwhile, a mixed solution of 9 parts of 2,2-azobis(2,4-dimethylvaleronitrile) dissolved in 110 parts of propylene glycol monomethyl ether acetate was added dropwise thereto over 5 hours. After the completion of dropwise addition, the internal temperature of the flask was kept at 85° C. for 3 hours, followed by cooling to room temperature to obtain a copolymer (resin B-1) solution having a type B viscosity (23° C.) of 70 mPas and containing 28.2% solid components. The produced copolymer had weight-average molecular weight Mw of 17000 and a distribution of 2.23. The resin B-1 thus obtained has the following structural units.

[Formula 49]

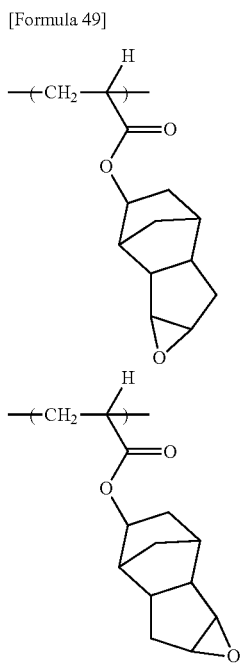

-continued

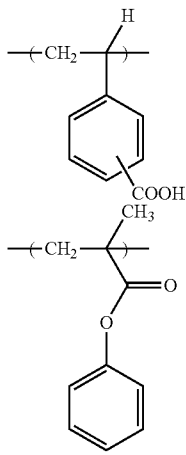

[Preparation of Colored Resin Composition]

Examples 5 and 6 and Comparative Example 2

Each colored resin composition was obtained by mixing the components according to the composition shown in Table 3 below.

TABLE 3

|  |  | Example 5 | Example 6 | Comparative Example 2 |
|---|---|---|---|---|
| Dye | I-13 | 12.9 | — | — |
|  | I-19 | — | 13 | — |
|  | I'-1 | — | — | 19.8 |
|  | I"-1 | 30 | 30 | 32 |
| Resin |  | 100 | 100 | 100 |
| Leveling agent |  | 0.1 | 0.1 | 0.1 |
| Solvent |  | 1437 | 1437 | 1524 |

The components shown in Table 3 will be given below.
Dye: I-13: dye represented by the formula (I-13)
I-19: dye represented by the formula (I-19)
I'-1: dye represented by the formula (I'-1)
I"-1: dye represented by the following formula produced by the method disclosed in Japanese Patent Laid-Open No. 2016-11419

Resin: resin B-1 (based on solid components) synthesized as described above
Leveling agent: MEGAFACE(R) F554 (manufactured by DIC Corp.)
Solvent: PGMEA(propylene glycol monomethyl ether acetate)
[Formation of Coating Film]

A glass substrate of 5 cm square (Eagle XG; manufactured by Corning Inc.) was coated with each colored resin composition prepared in Examples 5 and 6 and Comparative Example 2 by the spin coating method such that the film thickness after postbaking was 0.5 μm. Then, the coating was prebaked at 70° C. for 1 minute on a hot plate. Then, the coating was postbaked at 220° C. for 3 minutes on a hot plate to obtain a colored coating film.
<Chromaticity Evaluation>

The spectra of each obtained colored coating film were measured using a colorimeter (OSP-SP-200; manufactured by Olympus Corp.), and xy chromaticity coordinates (x, y) and tristimulus value Y in the CIE XYZ color system were measured using the characteristic function of a C light source. The results are shown in Table 4.

TABLE 4

|  | Film thickness [μm] | Chromaticity | | | Dye content |
|---|---|---|---|---|---|
|  |  | x | y | Y |  |
| Example 5 | 0.5 | 0.315 | 0.530 | 73 | 30% |
| Example 6 | 0.5 | 0.315 | 0.530 | 73 | 30% |
| Comparative Example 2 | 0.5 | 0.315 | 0.530 | 73 | 34% |

As shown in Table 4, an equivalent chromaticity value was obtained, albeit with a smaller dye content, in Examples 5 and 6 using the compound of the present invention, as compared with Comparative Example 2. As shown in Table 2, it is evident that the compounds represented by the formulas (I-1), (I-13), (I-7) and (I-19) in Examples 1 to 4 have higher absorbance at 640 nm than that of the compound represented by the formula (I'-1) in Comparative Example 1. It is therefore understood that the compounds represented by the formulas (I-1) and (I-7), as in the compounds represented by the formulas (I-13) and (I-19), can also reduce the content of the colorant compared with a conventional colorant in the case of achieving the same chromaticity value of the colored resin composition.

[Formula 50]

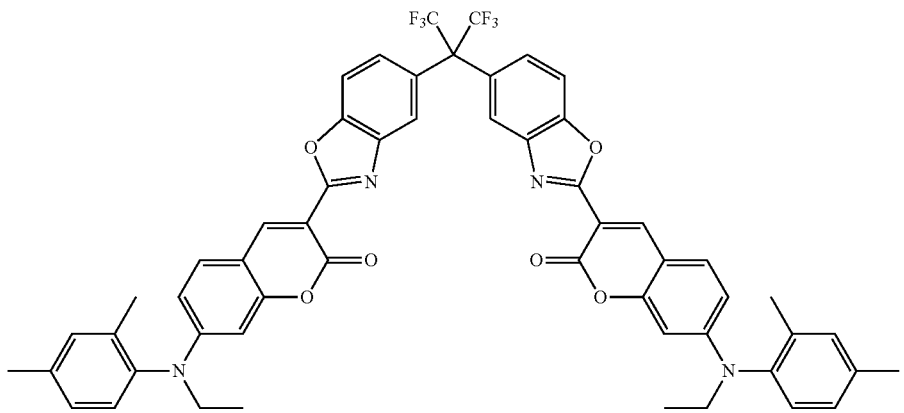

The invention claimed is:
1. A colored resin composition comprising a colorant and a resin, wherein the colorant is selected from the group consisting of compound (I-1), compound (I-7), compound (I-13) and compound (I-19):
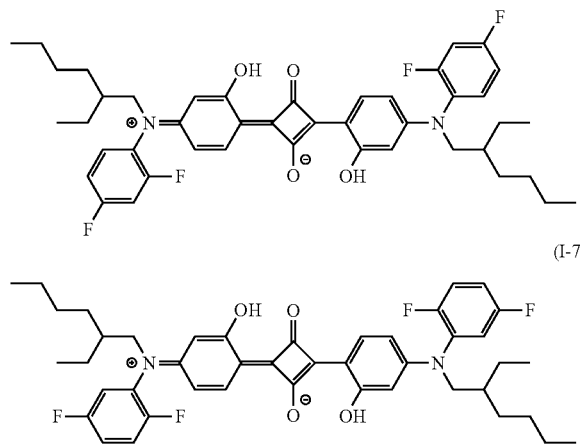
(I-1)
(I-7)
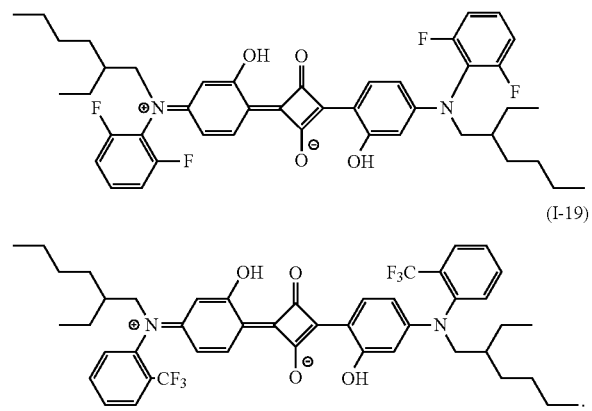
(I-13)
(I-19)
2. A color filter formed from a colored resin composition according to claim 1.
3. A solid-state imaging device comprising a color filter according to claim 2.
* * * * *